United States Patent [19]

An et al.

[11] Patent Number: 5,972,615
[45] Date of Patent: Oct. 26, 1999

[54] BIOMARKERS AND TARGETS FOR DIAGNOSIS, PROGNOSIS AND MANAGEMENT OF PROSTATE DISEASE

[75] Inventors: Gang An; Robert W. Vertri, both of Oklahoma City, Okla.

[73] Assignee: Urocor, Inc., Oklahoma City, Okla.

[21] Appl. No.: 09/010,398

[22] Filed: Jan. 21, 1998

[51] Int. Cl.$^6$ .............................. C12Q 1/68; C12P 19/34; C07H 21/04

[52] U.S. Cl. ............................ 435/6; 435/91.2; 435/91.5; 435/810; 536/23.1; 536/24.3; 536/24.31; 536/24.32; 536/24.37

[58] Field of Search .............................. 435/6, 91.2, 91.5, 435/810; 536/231, 24.3, 24.31, 24.32, 24.33

[56] References Cited

U.S. PATENT DOCUMENTS

| | | | |
|---|---|---|---|
| 5,236,844 | 8/1993 | Basset et al. | 435/320.1 |
| 5,459,037 | 10/1995 | Sutcliff et al. | 435/6 |
| 5,514,579 | 5/1996 | O'Hara et al. | 435/240.2 |
| 5,539,096 | 7/1996 | Babaï et al. | 536/24.3 |
| 5,677,125 | 10/1997 | Holt et al. | 435/6 |

FOREIGN PATENT DOCUMENTS

WO 94/10343  5/1994  WIPO .............................. C12Q 1/68

OTHER PUBLICATIONS

Umbas, Isaacs, Bringuier, Xue, Debruyne, Schalken, "Relation between aberrant α–catenin expression and loss of E–cadherin function in prostate cancer," *Int. J. Cancer (Pred. Oncol.)*, 74:374–377, 1997.

Umbas, Rainy, et al., "Expression of the Cellular Adhesion Molecule E–Cadherin Is Reduced or Absent in High–Grade Prostate Cancer", *Cancer Research*, 52:5104–5109, 1992.

U.S. Patent Application Serial No. 08/692,787.

Visakorpi, Tapio, et al., "Sensitive Detection of Chromosome Copy Number Abberations in Prostate Cancer by Fluorescence In Situ Hybridization", *Americal Journal of Pathology*, 145(3):624–630, 1994.

Webb, Karen S. Gerald H. Lin, "Urinary Fibronectin–Potential as a Biomarker in Prostatic Cancer", *Investigative Urology*, 17(5)401–404, 1980.

An et al., "Differential expression of full–length and a truncated Her–2/neu oncogene receptor in prostate cancer assessed using relative quantitative RT–PCR," *Molecular Urology*, 2(4):305–310, 1998.

Veltri et al., "Interleukin–8 serum levels in patients with benign prostatic hyperplasia and prostate cancer," *Urology*, 53(1):139–147, 1999.

Veltri et al., "The role of biopsy pathology, quantitative nuclear morphometry, and biomarkers in the preoperative prediction of prostate cancer staging and prognosis," *Seminars in Urologic Oncology*, 16(3):106–117, 1998.

Carter et al., "Prostate–specific membrane antigen is a hydrolase with substrate and pharmacologic characteristics of a neuropeptidase," *Proc. Natl. Acad. Sci. USA*, 93:749–753, 1996.

Dong et al., "KAI1, a metastasis suppressor gene for prostate cancer on human chromosome 11p11.2," *Science*, 268:884–886, 1995.

Huang et al., "Comparison of prostate secretory protein with prostate specific antigen and prostatic acid phosphatase as a serum biomarker for diagnosis and monitoring patients with prostate carcinoma," *Prostate*, 23:201–212, 1993.

Israeli et al., "Expression of the prostate–specific membrane antigen," *Cancer Res.*, 54:1807–1811, 1994.

Murphy et al., "Comparison of prostate specific antigen, prostate specific membrane antigen, and LNCaP–based enzyme–linked immunosorbent assays in prostatic cancer patients and patients with benign prostatic enlargement," *Prostate*, 26:164–168, 1995.

Murphy et al., "Evaluation and comparison of two new prostate carcinoma markers," *Cancer*, 78:809–818, 1996.

Partin and Oesterling, "The clinical usefulness of prostate specific antigen: update 1994," *J. Urol.*, 152:1358–1368, 1994.

Piironen et al., "Immunofluorometric assay for sensitive and specific measurement of human prostatic glandular kallikrein (hK2) in serum," *Clin. Chem.*, 42:1034–1041, 1996.

Silver et al., "Prostate–specific membrane antigen expression in normal and malignant human tissues," *Clin. Cancer Res.*, 3:81–85, 1997.

Dubbink et al, "Tissue–specific and androgen–regulated expression of human prostate specific transglutaminase", Biochem. J. 315:901–908, 1996.

Chopra et al, "Growth of human nondiploid primary prostate tumor epithelial cells in vitro", Cancer Res. 57:3688–3692, Sep. 1997.

Bej et al, "Amplification of nucleic acids by polymerase chain reaction (PCR) and other methods and their applications", Crit. Rev. Biochem. Mol. Biol. 26(3/4):301–334, 1991.

Leube et al, "Molecular characterization and expression of the stratification related cytokeratins 4 and 15", J. Cell Biol. 106:1249–1261, Apr. 1988.

Ulvsback et al, "Gene structure of semenogelin I and II", J. Biol. Chem. 267(25):18080–18084, Sep. 1992.

(List continued on next page.)

*Primary Examiner*—Jeffrey Fredman
*Attorney, Agent, or Firm*—Arnold, White & Durkee

[57] ABSTRACT

Disclosed are diagnostic techniques for the detection of human prostate disease. The invention relates particularly to probes and methods for evaluating the presence of RNA species that are differentially expressed in metastatic prostate cancer compared to normal human prostate, benign prostatic hyperplasia, and non-metastatic prostate cancer. The invention also relates to probes and methods for evaluating the presence of RNA species that are differentially expressed in the peripheral blood of individuals with the disease state compared to normal healthy individuals. Described are methods of therapeutic use for genes identified as differentially expressed in metastatic prostate cancer, and means for screening pharmaceuticals effective in treatment of prostate cancer.

23 Claims, No Drawings

OTHER PUBLICATIONS

Alcaraz, Antonio, et al., "Aneuploidy and Aneusomy of Chromosome 7 Detected by Fluorescence in Situ Hybridization Are Markers of Poor Prognosis in Prostate Cancer", *Cancer Research*, 54:3998–4002, 1994.

An et al., "Identification of novel gene markers in prostate disease by RNA fingerprinting," *Proceedings of the American Association for Cancer Research Annual Meeting*, 37(0):248, 1996. Abstract No. 1692.

An et al., "Sensitive, nonradioactive differential display method using chemiluminescent detection," *Biotechniques*, 20(3):342, 344, 346, 1996.

An, G., et al., Isolation of Genes differentially expressed in prostate cancer cells with metastatic potential by arbitrarily–primed differential analyses (ADA), *Proc. Amer. Assn. Canc. Res.*, 36:82 (#491), 1995.

Blok et al., "Isolation of cDNAs that are differentlially expressed between androgen–dependent and androgen–independent prostate carcinoma cells using differential display PCR", *Prostate*, 26(4):213–224, 1995.

Bookstein, Robert, et al., "Promoter deletion and loss of retinoblastoma gene expression in human prostate carcinoma", *Proc. Natl. Acad. Sci. USA*, 87:7762–7766, Oct., 1990.

Bookstein, Robert, et al., "Suppression of Tumorigenicity of Human Prostate Carcinoma Cells by Replacing a Mutated RB Gene", *Science*, 247:712–715, Feb., 1990.

Bova, G. Steven, et al., "Homozygous Deletion and Frequent Allelic Loss of Chromosome 8p22 Loci in Human Prostate Cancer", *Cancer Research*, 53:3869–3873, 1993.

Carter, Bob S., et al., "Allelic loss of chromosomes 16q and 10q in human prostate cancer", *Proc. Natl. Acad. Sci. USA*, 87:8751–8755, 1990.

Cookson, Reuter, Linkov, Fair, "Glutathione S–transferase (GST–$\pi$) class expression by immunohistochemistry in benign and malignant prostate tissue," *J. Urol.*, 157:673–676, 1997.

Dong, Suzuki, Pin, Bova, Schalken, Isaacs, Barrett, Isaacs, "Down–regulation of the KAI1 metastasis suppressor gene during the progression of human prostatic cancer infrequently involves gene mutation or allelic loss;" *Cancer Res.*, 56(19):4387–4390, 1996.

Greene et al., "Correlation of metastasis–related gene expression with metastatic potential in human prostate carcinoma cells implanted in nude mice using an in situ messenger RNA hybridization technique," *Am. J. Pathol.*, 150(5):1571–1582, 1997.

Hamdy et al., Circulating prostate specific antigen–positive cells correlate with metastatic prostate cancer, *British Journal of Urology*, 69(4):392–396, 1992.

International Search Report dated Mar. 20, 1998 (PCT/US97/22105) (UROC:014P).

Isaacs, William B., et al., "Molecular Biology of Prostate Cancer", *Seminars in Oncology*, 21(5):514–521, 1994.

Isaacs, William B., et al., "Wild–Type p53 Suppresses Growth of Human Prostate Cancer Cells Containing Mutant p53 Allels", *Cancer Research*, 51:4716–4720, 1991.

Ivanova and Belyavsky, "Identification of differentially expressed genes by restriction endonuclease–based gene expression fingerprinting," *Nucl. Acids Res.*, 23(15):2954–2958, 1995.

Luo et al., "A PCR differential screening method for rapid isolation of clones from a cDNA library," *Biotechniques*, 16(4):674–675, 1994.

Macoska, Jill A., et al., "Fluorescence in Situ Hybridization Analysis of 8p Allelic Loss and Chromosome 8 Instability in Human Prostate Cancer", *Cancer Research*, 54:3824–3830, 1994.

Matsushima et al., "Molecular cloning of a human monocyte–derived neutrophil chemotactic factor (MDNCF) and the induction of MDNCF mRNA by interleukin 1 and tumor necrosis factor," *J. Exp. Med.*, 167(6):1883–1893, 1988.

Morton, Ronald A., et al., "Reduction of E–Cadherin Levels and Deletion of the $\alpha$–Catenin Gene in Human Prostate Cancer Cells", *Cancer Research*, 53:3585–3590, 1993.

Murray, Taylor, McKay, Weaver, Ewen, Melvin, Burke, "The immunohistochemical localization of drug–metabolizing enzymes in prostate cancer," *J.Pathol.*, 177(2):147–152, 1995.

Nomura, "HumanRNA for KIAA0262 gene, complete cds," 1997, Database GenBank on STN, GenBack Accession No. D87451.

Paul, Ewing, Jarrard, Isaacs, "The cadherin cell–cell adhesion pathway in prostate cancer progression," *Brit. J. Urol.*, 79(Suppl.1):37–43, 1997.

Qiao, Liang, et al., "Effects of Suramin on Expression of Proliferation Associated Nuclear Antigens in DU–145 Prostate Carcinoma Cells", *Biochemical and Biophysical Research Communications*, 201(2):581–588, 1994.

Robson et al., Identificatin of prostatic androgen regulated genes using the differential display technique, *Proceedings of the American Association for Cancer Research Annual Meeting*, 36:266, 1995. Abstract No. 1589.

Schmid and Weissmann, "Induction of mRNA for a serine protease and a $\beta$–thromboglobulin–like protein in mitogen–stimulated human leukocytes," *J. Immunol.*, 139:250–256, 1987.

Takahashi, Satoru, et al., "Potential Markers of Prostate Cancer Aggressiveness Detected by Fluorescence in Situ Hybridization in Needle Biopsies", *Cancer Research*, 54:3574–3579, 1994.

BIOMARKERS AND TARGETS FOR DIAGNOSIS, PROGNOSIS AND MANAGEMENT OF PROSTATE DISEASE

BACKGROUND OF THE INVENTION

A. Field of the Invention

The present invention relates generally to the fields of detection, diagnosis and treatment of human disease states and methods relating thereto. More particularly, the present invention concerns probes and methods useful in diagnosing, identifying and monitoring the progression of diseases of the prostate through measurements of gene products. Also disclosed are various diagnostic and therapeutic methods and screening assays using the compositions of the invention.

B. Description of the Related Art

Carcinoma of the prostate (PCA) is the second-most frequent cause of cancer related death in men in the United States (Boring et al., 1993; Wingo et. al., 1997). The increased incidence of prostate cancer during the last decade has established prostate cancer as the most prevalent of all cancers (Carter and Coffey, 1990). Although prostate cancer is the most common cancer found in United States men, (approximately 210,000 newly diagnosed cases/year), the molecular changes underlying its genesis and progression remain poorly understood (Boring et al., 1993). According to American Cancer Society estimates, the number of deaths from PCA is increasing in excess of 8% annually.

An unusual challenge presented by prostate cancer is that most prostate tumors do not represent life threatening conditions. Evidence from autopsies indicate that 11 million American men have prostate cancer (Dbom, 1983). These figures are consistent with prostate carcinoma having a protracted natural history in which relatively few tumors progress to clinical significance during the lifetime of the patient. If the cancer is well-differentiated, organ-confined and focal when detected, treatment does not extend the life expectancy of older patients.

Unfortunately, the relatively few prostate carcinomas that are progressive in nature are likely to have already metastasized by the time of clinical detection. Survival rates for individuals with metastatic prostate cancer are quite low. Between these two extremes are patients with prostate tumors that will metastasize but have not yet done so. For these patients, surgical removal of their prostates is curative and extends their life expectancy. Therefore, determination of which group a newly diagnosed patient falls within is critical in determining optimal treatment and patient survival.

Although clinical and pathologic stage and histological grading systems (e.g., Gleason's) have been used to indicate prognosis for groups of patients based on the degree of tumor differentiation or the type of glandular pattern (Carter and Coffey, 1989; Diamond et al., 1982; O'Dowd et al., 1997), these systems do not predict the progression rate of the cancer. While the use of computer-system image analysis of histologic sections of primary lesions for "nuclear roundness" has been suggested as an aide in the management of individual patients (Diamond et al., 1982), this method is of limited use in studying the progression of the disease.

Recent studies have identified several recurring genetic changes in prostate cancer including: allelic loss (particularly loss of chromosome 8p and 16q) (Bova. et al., 1993; Macoska et al, 1994; Carter et al, 1990), generalized DNA hypermethylation, (Isaacs et al., 1994), point mutations or deletions of the retinoblastoma (Rb) and p53 genes (Bookstein et al., 1990a; Bookstein et al., 1990b; Isaacs et al., 1991), alterations in the level of certain cell-cell adhesion molecules (i.e., E-cadherin/alpha-catenin)(Carter et al., 1990); Morton et al., 1993a; Morton et al., 1993b; Umbas et al., 1992), and aneuploidy and aneusomy of chromosomes detected by fluorescence in situ hybridization (FISH), particularly chromosomes 7 and 8 (Macoska et al., 1994; Visakorpi et al., 1994; Takahashi et al., 1994; Alcaraz et al., 1994).

The analysis of DNA content/ploidy using flow cytometry and FISH has been demonstrated to have utility predicting prostate cancer aggressiveness (Pearsons et al., 1993; Macoska et al., 1994; Visakorpi et al., 1994; Takahashi et al., 1994; Alcaraz et al., 1994; Pearsons et al., 1993; Veltri et al., 1994), but these methods are expensive, time-consuming, and the latter methodology requires the construction of centromere-specific probes for analysis.

Specific nuclear matrix proteins have been reported to be associated with prostate cancer. (Partin et al., 1993). However, these protein markers apparently do not distinguish between benign prostate hyperplasia and prostate cancer. (Partin et al., 1993). Unfortunately, markers which cannot distinguish between benign and malignant prostate tumors are of little value.

A recent development in this field was the identification of prostate metastasis suppresser genes, KAI1, E-cadherin, alpha-catenin and GST-pi (Dong et al., 1995; Carter et al., 1990; Morton et al., 1993a; Morton et al., 1993b; Umbas et al., 1992; Cookson et al., 1997; Lee et al., 1997). Insertion of wild-type KAI1 gene into a rat prostate cancer line caused a significant decrease in metastatic tumor formation (Dong et al., 1995). However, detection of KAI1, E-cadherin, alpha-catenin, and GST-pi mutations are dependent upon direct sampling of mutant prostate cells (Dong et al., 1996; Umbas et al, 1992; Cookson et al, 1997; Murray et al., 1995). Thus, either a primary prostate tumor must be sampled or else sufficient transformed cells must be present in blood, lymph nodes or other tissues to detect the missing or abnormal gene. Further, the presence of a deleted gene may frequently be masked by large numbers of untransformed cells that may be present in a given tissue sample.

The most commonly utilized current tests for prostate cancer are digital rectal examination (DRE) and analysis of serum prostate specific antigen (PSA). Although PSA has been widely used as a clinical marker of prostate cancer since 1988 (Partin and Oesterling, 1994), screening programs utilizing PSA alone or in combination with digital rectal examination have not been successful in improving the survival rate for men with prostate cancer (Partin and Oesterling, 1994). While PSA is specific to prostate tissue, it is produced by normal and benign as well as malignant prostatic epithelium, resulting in a high false-positive rate for prostate cancer detection (Partin and Oesterling, 1994).

Other markers that have been used for prostate cancer detection include prostatic acid phosphatase (PAP) and prostate secreted protein (PSP). PAP is secreted by prostate cells under hormonal control (Partin and Oesterling, 1994). It has less specificity and sensitivity than does PSA. As a result, it is used much less now, although PAP may still have some applications for monitoring metastatic patients that have failed primary treatments. In general, PSP is a more sensitive biomarker than PAP, but is not as sensitive as PSA (Huang et al., 1993). Like PSA, PSP levels are frequently elevated in patients with BPH as well as those with prostate cancer.

Another serum marker associated with prostate disease is prostate specific membrane antigen (PSMA) (Horoszewicz et al., 1987; Carter et al., 1996; Murphy et al., 1996). PSMA is a Type II cell membrane protein and has been identified as Folic Acid Hydrolase (FAH) (Carter et al., 1996). Antibodies against PSMA react with both normal prostate tissue and prostate cancer tissue (Horoszewicz et al., 1987). Murphy et al. (1995) used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (Silver et al., 1997) and is reported to be more abundant in the blood of metastatic cancer patients (Murphy et al., 1996). PSMA messenger RNA (mRNA) is down-regulated 8–10 fold in the LNCaP prostate cancer cell line after exposure to 5-α-dihydroxytestosterone (DHT) (Israeli et al., 1994).

A relatively new potential biomarker for prostate cancer is human kallekrein 2 (HK2) (Piironen et al., 1996). HK2 is a member of the kallekrein family that is secreted by the prostate gland. In theory, serum concentrations of HK2 may be of utility in prostate cancer detection or diagnosis, but the usefulness of this marker is still being evaluated.

There remain, however, deficiencies in the art with respect to the identification of the genes linked with the progression of prostate diseases, including prostate cancer, and metastatic prostate cancer, the development of diagnostic methods to monitor disease progression, and the development of therapeutic methods and compositions to treat prostate diseases and cancers. The identification of genes which are differentially expressed in prostate diseases would be of considerable importance in the development of a rapid, inexpensive method to diagnose prostate diseases, including cancer. The identified genes would also be useful in therapeutic compositions, or in screening assays for therapeutic compounds.

SUMMARY OF THE INVENTION

The present invention provides unique markers that are shown herein to be useful in diagnosing or identifying a subject with a metastatic prostate cancer condition. The metastatic cancer markers of the present invention are shown to be absent or down regulated in a metastatic state, but are found in the prostate tissue or serum of subjects known not have metastatic prostate cancer. The markers identified herein are shown to distinguish a condition of metastatic prostate cancer from a condition of normal (healthy), benign hyperplasia and confined prostate cancer. Diagnosis of the metastatic state as disclosed herein may include but is not limited to examination for the presence of specific markers in a prostate tissue sample, in a serum sample or both from subjects suspected of having a prostate disease. The ability to distinguish different stages of prostate disease has important implications for treatment or management of the subject's condition.

The identification of markers, or of differential expression of certain genes or gene products in the practice of the invention may take any of several forms. For example, one may detect expression or lack of expression of a mRNA or other RNA product, or one may detect the expression or lack of expression of a protein or polypeptide in a certain cell, tissue or other biological sample of a subject. Methods for identifying such RNA species and encoded proteins are described. These RNA species and the corresponding encoded protein species have utility, for example, as markers of prostate disease state and as targets for therapeutic intervention in prostate disease.

The identified markers of prostate disease can in turn be used to design specific nucleic acid probes and primers, for example for the direct hybridization to a target mRNA or for use as primers in amplifying a target to be identified or quantified using an enzyme dependent amplification. When used in combination with nucleic acid hybridization and amplification procedures, these probes and primers permit the rapid analysis of prostate biopsy core specimens, serum samples, etc. This will assist physicians in diagnosing prostate disease and metastatic prostate disease in particular, and in determining optimal treatment or disease management courses for individuals with various stages of prostate disease. The same probes and primers may also be used for in situ hybridization or in situ PCR detection and diagnosis of prostate disease.

The present invention may be described in certain embodiments as a method of diagnosing a metastatic prostate disease state in a subject, comprising the steps of obtaining a test sample from prostate tissue or serum or both of said subject and detecting down-regulation of expression of a metastatic prostate disease marker gene selected from prostate-specific transglutaminase, cytokeratin 15, or semenogelin II or a combination thereof in the sample. Down-regulation may be indicated by lack of a positive response to a standard assay or test. Down-regulation may also be determined by a direct comparison of quantity of expression of one or more markers in a test sample compared to quantity of expression of the same one or more markers in a control sample obtained from prostate tissue or serum or both of one or more individuals known not to have metastatic prostate disease. The control sample may be from an individual or from a population pool that are known to have no prostate disease, BPH or even confined prostate cancer. In such a comparison, a difference in quantity of expression in the test sample compared to the control sample is indicative of a metastatic prostate disease state. It is also an embodiment of the invention that the quantity of expression of the disclosed marker or markers would be determined and compared to known levels of expression in normal tissue or in tissue from subjects in other states of prostate disease.

The methods of the present invention preferably would use as markers, products of a prostate-specific transglutaminase gene, a cytokeratin 15 gene, or a semenogelin II gene. In certain embodiments of these methods, the prostate-specific transglutaminase gene includes another molecule having the sequence designated herein as SEQ ID NO:1 or its complement, the cytokeratin 15 gene includes another molecule having the sequence designated herein as SEQ ID NO:2 or its complement and semenogelin II gene includes another molecule having the sequence designated herein as SEQ ID NO:3 or its complement, and/or the sequence designated herein as SEQ ID NO:14 or its complement, or polypeptide products expressed from any of these nucleic acid molecules.

In certain embodiments, the present invention would include obtaining or detecting ribonucleic acids from the samples, both test samples and possibly control samples. Ribonucleic acids from a biological sample may be obtained by any means known in the art, and would typically entail a total RNA preparation. The RNA so obtained is then detected, for example, by contact with a probe that hybridizes under high stringency conditions with an RNA product of the marker genes to obtain a hybridized product. One detection method commonly used by those of skill in the art is Northern hybridization, and it is a preferred method of detection, diagnosis, and/or prognosis of prostate disease or cancer.

By high stringency conditions, is meant conditions under which the probe specifically hybridizes to a target sequence in an amount that is detectably stronger than non-specific hybridization. High stringency conditions, then, would be conditions which would distinguish a polynucleotide with an exact complementary sequence, or one containing only a few scattered mismatches from a random sequence that happened to have a few small regions (3–10 bases, for example) that matched the probe. Such small regions of complementarity, are more easily melted than a full length complement of 14–17 or more bases and high stringency hybridization makes them easily distinguishable. Relatively high stringency conditions would include, for example, low salt and/or high temperature conditions, such as provided by about 0.02 M to about 0.10 M NaCl or the equivalent, at temperatures of about 50° C. to about 70° C. Such high stringency conditions tolerate little, if any, mismatch between the probe and the template or target strand, and would be particularly suitable for detecting expression of specific metastatic prostate disease markers. It is generally appreciated that conditions can be rendered more stringent by the addition of increasing amounts of formamide.

In the practice of this embodiment, one may use a nucleic acid segment that is complementary to the full length of the mRNA encoded by a marker gene, or one may use a smaller segment that is complementary to a portion of the marker RNA. Such smaller segments may be from about 14, about 15, about 16, about 17, about 18, about 19, about 20, about 21, about 22, about 23, about 24, about 25, about 25, about 30, about 50, about 75, about 100 or even several hundred bases in length and may be contained in larger segments that provide other functions such as promoters, restriction enzyme recognition sites, or other expression or message processing or replication functions. In preferred embodiments such probes are designed to selectively hybridize to a prostate-specific transglutaminase, cytokeratin 15, or semenogelin II mRNA or product thereof. A product thereof would include a DNA or RNA strand that is complementary to the mRNA and thus a useful probe would include both the sense and antisense orientations of a particular sequence. Also preferred are the use of probes or primers that are designed to selectively hybridize to a nucleic acid segment having a sequence of SEQ ID NO:1, SEQ ID NO:2 or SEQ ID NO:3 or the complements thereof.

The methods of the present invention may also include determining the amount of hybridized product. Such determination may be by direct detection of a labeled hybridized probe, such as by use of a radioactive, fluorescent or other tag oil the probe, or it may be by use of an amplification of a target sequence, and quantification of the amplified product. A preferred method of amplification is a reverse transcriptase polymerase chain reaction (RT-PCR) as described herein. RT-PCR is a preferred method of detection, diagnosis, and/or prognosis of prostate disease or cancer. In the practice of such a method, amplification may comprise contacting the target ribonucleic acids with a pair of amplification primers designed to amplify a prostate-specific transglutaminase, cytokeratin 15, or semenogelin II mRNA, or even contacting the ribonucleic acids with a pair of amplification primers designed to amplify a nucleic acid segment comprising the nucleic acid sequence or complement of SEQ ID NO:1, SEQ ID NO:2 or SEQ ID NO:3.

The type or amount of prostate-specific transglutaminase, cytokeratin 15, and/or semenogelin II may be determined by means of a molecular biological assay to determine the type or amount of a nucleic acid that encodes prostate-specific transglutaminase, cytokeratin 15, and/or semenogelin II. Such molecular biological assays will often comprise a direct or indirect step that allows a determination of the sequence of at least a portion of the prostate-specific transglutaminase, cytokeratin 15, and/or semenogelin II-encoding nucleic acid, which sequence can be compared to a wild-type prostate-specific transglutaminase, cytokeratin 15, and/or semenogelin II sequence or expression of wild-type sequence, such as SEQ ID NO:1, SEQ ID NO:2, SEQ ID NO:3, or SEQ ID NO:14 or another acceptable normal allelic or polymorphic sequence.

It is contemplated that prostate-specific transglutaminase, cytokeratin 15, and/or semenogelin II sequences diagnostic or prognostic for a particular disease may comprise at least one point mutation, deletion, translocation, insertion, duplication or other aberrant change. Diagnostic RFLPs are thus also contemplated. RNase protection assays (RPA) may also be employed in certain embodiments, and is a preferred method of detection, diagnosis, and/or prognosis of prostate disease or cancer.

Diagnostic methods may be based upon the steps of obtaining a biological sample from a subject or patient, contacting sample nucleic acids from the biological sample with an isolated prostate-specific transglutaminase, cytokeratin 15, and/or semenogelin II nucleic acid segment under conditions effective to allow hybridization of substantially complementary nucleic acids, and detecting, and optionally further characterizing, the hybridized complementary nucleic acids thus formed.

The methods may involve in situ detection of sample nucleic acids located within the cells of the sample. The sample nucleic acids may also be separated from the cell prior to contact. The sample nucleic acids may be DNA or RNA.

The methods may involve the use of isolated prostate-specific transglutaminase, cytokeratin 15, and/or semenogelin II nucleic acid segments that comprises a radio, enzymatic or fluorescent detectable label, wherein the hybridized complementary nucleic acids are detected by detecting the label. In preferred embodiments such probes are designed to selectively hybridize to a prostate-specific transglutaminase, cytokeratin 15, or semenogelin II mRNA or product thereof. A product thereof would include a DNA or RNA strand that is complementary to the mRNA and thus a useful probe would include both the sense and antisense orientations of a particular sequence. Also preferred are the use of probes or primers that are designed to selectively hybridize to a nucleic acid segment having a sequence of SEQ ID NO:1, SEQ ID NO:2, SEQ ID NO:3, SEQ ID NO:14 or the complements thereof.

In the practice of the invention, some methods may involve detection of expression of a polypeptide product of a marker gene such as a prostate-specific transglutaminase, cytokeratin 15, or semenogelin II gene, and particularly the expression product encoded by SEQ ID NO:1, SEQ ID NO:2, SEQ ID NO:3, or SEQ ID NO:14. Such detection may be by any means known in the art and may include an immunoassay, an immunoaffinity purification or detection, an ELISA, or an radioimmunoassay, for example.

The present invention may also be described in certain embodiments as a kit for use in detecting a metastatic prostate disease state through testing of a biological sample. A representative kit may comprise one or more nucleic acid segments as described above that selectively hybridize to a prostate-specific transglutaminase, cytokeratin 15, or semenogelin II mRNA and a container for each of the one or more nucleic acid segments. In certain embodiments the nucleic acid segments may be combined in a single tube. In certain embodiments the nucleic acid segments would be designed lo selectively hybridize to a nucleic acid segment that includes the sequence or complement of SEQ ID NO:1, SEQ ID NO:2, SEQ ID NO:3, or SEQ ID NO:14. In further embodiments, the nucleic acid segments may also include a pair of primers for amplifying the target mRNA. Such kits may also include any buffers, solutions, solvents, enzymes, nucleotides, or other components for hybridization, amplification or detection reactions. Preferred kit components include reagents for RT-PCR, in situ hybridization, Northern analysis and/or RPA.

In certain embodiments the kit for use in detecting a metastatic prostate disease state in a biological sample may comprise an antibody which immunoreacts with a prostate-specific transglutaminase, cytokeratin 15, or semenogelin II polypeptide and a container for the antibody. Such an antibody may be a polyclonal or a monoclonal antibody and may be included in a kit with reagents, secondary antibodies, labeling means, or other components for polypeptide detection including, but not limited to an ELISA kit.

The invention further comprises the prognosis and/or diagnosis of prostate disease by measuring the amounts of nucleic acid amplification products formed as above. The amounts of nucleic amplification products identified in an individual patient may be compared with groups of normal individuals or individuals with an identified disease state. Diagnosis may be accomplished by finding that the patient's levels of disease state markers fall within the normal range, or within the range observed in individuals with the disease state. Further comparison with groups of individuals of varying disease state progression, such as metastatic vs. non-metastatic cancer, may provide a prognosis for the individual patient. The invention further broadly comprises kits for performing the above-mentioned procedures, containing amplification primers and/or hybridization probes.

Certain embodiments of the present invention comprise the use of antibodies specific to the proteins and peptides encoded by SEQ ID NO:1, SEQ ID NO:2, SEQ ID NO:3, and SEQ ID NO:14. Such antibodies may be useful for diagnostic and prognostic applications in detecting the disease state, by comparing a patient's levels of prostate disease marker expression to expression of the same markers in normal or non-metastatic individuals. In certain embodiments production of monoclonal or polyclonal antibodies can be induced by the use of the aforementioned proteins and peptides as antigens. Such antibodies may in turn be used to detect expressed proteins as markers for human disease states. The levels of such proteins present in the peripheral blood or prostate tissue sample of a patient may be quantified by conventional methods. Antibody-protein binding may be detected and quantified by a variety of means known in the art, such as labeling with fluorescent or radioactive ligands. The invention further comprises kits for performing the above-mentioned procedures, wherein such kits contain antibodies specific for the aforementioned proteins and peptides.

Another aspect of the present invention comprises the detection and diagnosis of disease states, including BPH and prostate cancer, or metastatic prostate cancer by combining measurement of levels of two or more disease state markers. An embodiment of the invention comprises combining measurement of SEQ ID NO:1, SEQ ID NO:2, SEQ ID NO:3, and SEQ ID NO:14 gene expression products with other markers of prostate disease, such as PSA, PAP, HK2, $PSP_{94}$ and PSMA, as exemplified in U.S. patent application Ser. No. 08/692,787, incorporated herein by reference. Yet another aspect of the present invention comprises kits for detection and measurement of the levels of two or more disease state markers in biological samples. The skilled practitioner will realize that such kits may incorporate a variety of methodologies for detection and measurement of disease state markers, including but not limited to oligonucleotide probes, primers for nucleic acid amplification, antibodies which bind specifically to protein products of disease state marker genes, and other proteins or peptides which bind specifically to disease state marker gene products.

In one aspect, the present invention encompasses kits for use in detecting a prostate disease state in a biological sample. Such a kit may comprise one or more pairs of primers for amplifying nucleic acids corresponding to prostate disease marker genes. The kit may further comprise samples of total mRNA derived from tissue of subjects in various physiological states, such as normal, BPH, confined tumor and metastatically progressive tumor, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting a prostate disease state by analysis of a biological sample comprising oligonucleotide probes effective to bind with high affinity to markers of prostate disease in a Northern blot assay and containers for each of these probes. In a further embodiment, the invention encompasses a kit for use in detecting a prostate disease state by analysis of a biological sample comprising antibodies specific for proteins encoded by the nucleic acid markers of prostate disease identified in the present disclosure.

Where a decrease in the amount or activity of prostate specific transglutaminase, cytokeratin 15, and/or semenogelin II in a subject proves to be diagnostic of a prostate disease such as metastatic prostate cancer, the present invention also provides methods of treating prostate disease, comprising administering to such a patient with prostate disease a therapeutically effective amount of a pharmaceutically acceptable solution containing a prostate specific transglutaminase, cytokeratin 15, and/or semenogelin II composition. These treatments may comprise administering a composition containing prostate specific transglutaminase, cytokeratin 15, and/or semenogelin II protein or peptides, or compositions containing prostate specific transglutaminase, cytokeratin 15, and/or semenogelin II DNA segments or recombinant vectors that express prostate specific transglutaminase, cytokeratin 15, and/or semenogelin II proteins or peptides. Such vectors may be administered to a subject in vivo, i.e. through intravenous administration, or ex vivo by transfection into isolated cells that are cultured and then infused into the subject. Such cells are preferably homologous cells, i.e. derived from tissue or serum of the patient, or they may include heterologous cells.

Vectors that may be used include, but are not limited to, plasmid vectors, naked DNA, viral vectors, including retroviral and DNA vectors, such as adenovirus, adeno-associated virus, vaccinia virus, sindbis virus, cytomegalovirus, herpes simplex virus, defective hepatitis B viruses, and any other vector or vector system described herein or known in the art. Vectors may be transfected into host cells by means including, but not limited to, viral infection, calcium phosphate precipitation, DEAE-dextran, electroporation, direct microinjection, DNA-loaded liposomes and lipofectamine-DNA complexes, cell sonication, gene bombardment using high velocity microprojectiles, polycations, and receptor-mediated transfection, or any other means described herein or known in the art. Methods of treatment may also include administering modulators of prostate specific transglutaminase, cytokeratin 15, and/or semenogelin II enzyme transcription, translation, stability or activity.

An aspect of the present invention is a cell-based assay for identifying compounds which affect prostate-specific transglutaminase, cytokeratin 15, and semenogelin II production. Specifically, the assay comprises culturing a cell containing an expression vector comprising a DNA sequence encoding a prostate-specific transglutaminase, cytokeratin 15, and/or semenogelin II promoter operatively linked to a reporter gene under conditions which permit expression and quantitative assay of the reporter gene. The cultured cell is incubated with compounds suspected of possessing regulatory activity for production of prostate-specific transglutaminase, cytokeratin 15, and/or semenogelin II. These regulatory compounds are identified by their ability to modulate the expression of the reporter gene and thereby affect the production of the assayable product of the reporter gene. In certain aspects of the invention the terms "modulation", "modulate", "affect", "regulate", and "alter" may mean an increase or decrease the expression of a gene or a gene product's activity.

In a general embodiment, the present invention provides a method for screening a compound for its ability to affect prostate-specific transglutaminase, cytokeratin 15, and/or semenogelin II production in mammalian cells. The method comprises the following steps: providing an expression construct comprising a prostate-specific transglutaminase, cytokeratin 15, and/or semenogelin II promoter and a reporter gene, wherein the reporter gene is under transcriptional control of the promoter, transfecting the mammalian cells with the expression construct, contacting the transfected cell with the compound; and identifying a compound that regulates expression of the reporter gene from the promoter. In a preferred embodiment, the reporter gene is selected from the group consisting of firefly luciferase, chloramphenicol acetyl transferase, β-galactosidase, green fluorescent protein, human growth hormone, alkaline phosphatase and β-glucuronidase.

In a further preferred embodiment, the promoter for prostate-specific transglutaminase, cytokeratin 15, and/or semenogelin II is derived from the native human prostate-specific transglutaminase, cytokeratin 15, and semenogelin II promoter. The present invention provides methods of identifying and isolating prostate-specific transglutaminase, cytokeratin 15, and/or semenogelin II promoter regions for the aforementioned screening methods. Additionally, promoter sequence for human semenogelin II is described in GenBank Accession number M81651.

The present invention may be used to screen a compound for its ability to regulate prostate-specific transglutaminase, cytokeratin 15, and/or semenogelin II production in human cells. A particularly useful cell population to use in screening for prostate-specific transglutaminase, cytokeratin 15, and/ or semenogelin II stimulation is human tumor cells. Most notably, the present invention is useful in screening compounds which affect prostate-specific transglutaminase and/ or cytokeratin 15 production in prostate cancer cells. The present invention is also useful in screening compounds which affect semenogelin II production in lymphocyte cancer cells. A useful prostate cancer cell population in which to perform screening is LNCaP prostate cancer cell line. Other preferred cell lines include DU145, PC-3, C4-2, C4-2Ln and C4-2B (Chung et al., 1994, Cancer Research, 54:2577–2581.

In another embodiment, the present invention provides compounds that affect prostate-specific transglutaminase, cytokeratin 15, and semenogelin II production in mammalian cells. This compound is identified by the method comprising the steps of: providing an expression construct comprising a prostate-specific transglutaminase, cytokeratin 15, and semenogelin II promoter and a reporter gene, wherein the reporter gene is under transcriptional control of the promoter, transfecting the mammalian cells with the expression construct, contacting the transfected cell with the compound, and identifying a compound that regulates expression of the reporter gene from the promoter.

Preferably, the compound is identified from a small molecule chemical library, a peptide library, or from a collection of natural products.

Finally, yet a another embodiment of the present invention provides a method of regulating prostate-specific transglutaminase, cytokeratin 15, and/or semenogelin II production in mammalian cells. This method comprises the step of contacting a cell with a compound that affects prostate-specific transglutaminase, cytokeratin 15, and/or semenogelin II production in the cell.

DESCRIPTION OF ILLUSTRATIVE EMBODIMENTS

The present invention concerns the early detection, diagnosis, prognosis and treatment of prostate diseases, such as prostate cancer or benign prostatic hyperplasia (BPH). Markers of prostate disease, in the form of nucleic acid sequence isolated from human prostate enriched tissue, are disclosed. These markers are indicators of malignant transformation of prostate tissues and are diagnostic of the potential for metastatic spread of prostate tumors.

Those skilled in the art will realize that the nucleic acid sequences disclosed will find utility in a variety of applications in prostate disease detection, diagnosis, prognosis and treatment. Examples of such applications within the scope of the present invention comprise amplification of markers of prostate disease using specific primers, detection of markers of prostate disease by hybridization with oligonucleotide probes, incorporation of isolated nucleic acids into vectors, expression of RNA, peptides or polypeptides from the vectors, development of immunologic reagents corresponding to marker encoded products, and therapeutic treatments of prostate disease using expression vectors, or expression activators specific for the identified prostate disease markers.

A. Nucleic Acids

As described herein, an aspect of the present disclosure is three markers of prostate disease, identified by Southern Differential Hybridization, Northern analysis, and quantitative RT-PCR. These include the nucleic acid products of prostate-specific transglutaminase (GenBank accession #s L34840, I20492), cytokeratin 15 (GenBank accession #X07696), and semenogelin II (GenBank accession #M81652 and M81651). The present invention is the first report of under-expression of these gene products in metastatic prostate cancer.

In one embodiment, the nucleic acid sequences disclosed herein will find utility as hybridization probes or amplification primers. These nucleic acids may be used, for example, in diagnostic evaluation of tissue or serum samples. In certain embodiments, these probes and primers consist of oligonucleotides. Such oligonucleotides are of sufficient length to provide specific hybridization to a RNA or DNA target derived from a tissue or serum sample. The oligos are typically will be 10–20 nucleotides, but may be longer. Longer sequences, e.g., 30, 40, 50, 100, 500 nucleotides and even up to full length, as disclosed in SEQ ID NO:1, SEQ ID NO:2, SEQ ID NO:3, or SEQ ID NO:14 are preferred for certain embodiments.

Nucleic acid molecules having contiguous stretches of about 10, 15, 17, 20, 30, 40, 50, 60, 75 or 100 or 500 nucleotides homologous to a sequence selected from SEQ ID NO:1, SEQ ID NO:2, SEQ ID NO:3, and SEQ ID NO:14 are contemplated. Molecules that bind to these sequences under high stringency conditions also are contemplated. These probes will be useful in a variety of hybridization embodiments, such as Southern, Northern blotting and in situ hybridization. In some cases, it is contemplated that probes may be used that hybridize to multiple target sequences without compromising their ability to effectively diagnose disease.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defining all primers can be proposed:

$n$ to $n+y$ where n is an integer from 1 to the last number of the sequence and y is the length of the primer minus one (9 to 19), where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of RNA from tissue or serum. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

The following codon chart may be used, in a site-directed mutagenic scheme, to produce nucleic acids encoding the same or slightly different amino acid sequences of a given nucleic acid:

TABLE 1

Codon Usage

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It is understood that this disclosure is not limited to the particular probes disclosed herein and particularly is intended to encompass at least isolated nucleic acids that are hybridizable to nucleic acids comprising the disclosed sequences or that are functional sequence analogs of these nucleic acids. For example, a nucleic acid of partial sequence may be used to quantify the expression of a structurally-related gene or the full length genomic or cDNA clone from which it is derived.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

B. Encoded Proteins

The metastatic cancer marker genes described herein can be inserted and expressed in any number of different recombinant DNA expression systems to generate large amounts of the polypeptide product, which can then be purified and used to vaccinate animals to generate antisera for use in the practice of the present invention.

Examples of expression systems known to the skilled practitioner in the art include bacteria such as *E. coli*, yeast such as *Pichia pastoris*, baculovirus, and mammalian expression systems such as in Cos or CHO cells. A complete gene can be expressed or, alternatively, fragments of the gene encoding antigenic portions of polypeptide can be produced.

In certain applications of the invention, the gene sequence encoding the polypeptide is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli*, as it leads to the production of insoluble aggregates which are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences may not, therefore, prove useful in in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene.

Computer sequence analysis may be used to determine the location of the predicted major antigenic determinant epitopes of the polypeptide. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences may be found on the surface of proteins and are, therefore, likely to act as antigenic determinants.

Once this analysis is made, polypeptides may be prepared which contain at least the essential features of the antigenic determinant and which may be employed in the generation of antisera against the polypeptide. Minigenes or gene fusions encoding these determinants may be constructed and inserted into expression vectors by standard methods, for example, using PCR cloning methodology.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (St.9) cells by standard protocols, and the cells are cultured and processed to produce the recombinant antigen. See Summers et al., A Manual of Methods for Baculovirus Vectors and Insect Cell Culture Procedures, Texas Agricultural Experimental Station; U.S. Pat. No. 4,215,051 (incorporated by reference).

As an alternative to recombinant polypeptides, synthetic peptides corresponding to the antigenic determinants may be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

Amino acid sequence variants of the polypeptide may also be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of site-directed mutagenesis such as those described herein for removing the transmembrane sequence.

Amino acid sequence variants of the polypeptide may be substitutional, insertional or deletion variants. Deletion variants lack one or more residues of the native protein which are not essential for function or immunogenic activity, and are exemplified by the variants lacking a transmembrane sequence. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also may include hybrid proteins containing sequences from other proteins and polypeptides which are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

Major antigenic determinants of the polypeptide may be identified by an empirical approach in which portions of the gene encoding the polypeptide are expressed in a recombinant host, and the resulting proteins tested for their ability to elicit an immune response. For example, PCR may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then allows the location of the antigenic determinants of the polypeptide.

Another method for the preparation of the polypeptides according to the invention is the use of peptide mimetics. Mimetics are peptide-containing molecules which mimic elements of protein secondary structure. See, for example, Johnson et al., 1993. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within a polypeptide may be predicted by computer-based algorithms as discussed herein. Once the component amino acids of the turn are determined, peptide mimetics may be constructed to achieve a similar spatial orientation of the essential elements of the amino acid side chains.

C. Preparation of Antibodies Specific for Encoded Proteins
  1. Expression of Proteins from Cloned cDNAs The cDNA species specified in SEQ ID NO:1, SEQ ID NO:2 and SEQ ID NO:3 may be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the isolated cDNA species or the nucleic acid sequences for the disclosed prostate disease marker genes.

Both cDNA and genomic sequences are suitable for eukaryotic expression, as the host cell will generally process the genomic transcripts to yield functional mRNA for translation into protein. For example, the semenogelin II genomic sequence specified in SEQ ID NO:14 may be expressed in a eukaryotic system by techniques generally known to those of skill in the art. In addition, it is possible to use partial sequences for generation of antibodies against discrete portions of a gene product, even when the entire sequence of that gene product remains unknown. Computer programs are available to aid in the selection of regions which have potential immunologic significance. For example, software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene. The heterologous gene may be inserted into the host genome or maintained on an episome.

To express a recombinant encoded protein or peptide, whether mutant or wild-type, in accordance with the present invention one would prepare an expression vector that comprises one of the claimed isolated nucleic acids under the control of, or operatively linked to, one or more promoters. To bring a coding sequence "under the control of" a promoter, one positions the 5' end of the transcription initiation site of the transcription reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors, in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographa californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g, Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase (Wigler et al., 1977), hypoxandine-guanine phosphoribosyltransferase(Szybalska et al., 1962) and adenine phosphoribosyltransferase genes (Lowy et al., 1980), in tk-, hgprt- or aprt- cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

It is contemplated that the isolated nucleic acids of the invention may be "overexpressed", i.e., expressed in increased levels relative to its natural expression in human prostate cells or peripheral blood cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human prostate cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide" as used herein, is intended to refer to a composition, isolable from other components, wherein the protein or peptide is purified to any degree relative to its naturally-obtainable state, i.e., in this case, relative to its purity within a prostate cell extract. A purified protein or peptide therefore also refers to a protein or peptide, free from the environment in which it may naturally occur.

Generally, "purified" will refer to a protein or peptide composition which has been subjected to fractionation to remove various other components, and which composition substantially retains its expressed biological activity. Where the term "substantially purified" is used, this will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide may vary, sometimes significantly, with different conditions of SDS/PAGE (Capaldi et al., 1977). It will therefore be appreciated that under differing electrophoresis conditions, the apparent molecular weights of purified or partially purified expression products may vary.

3. Antibody Generation

For some embodiments, it will be desirable to produce antibodies that bind with high specificity to the polypeptide product(s) of an isolated nucleic acid selected from SEQ ID NO:1, SEQ ID NO:2, SEQ ID NO:3 and SEQ ID NO:14 or the disclosed prostate disease marker genes: prostate specific transglutaminase, cytokeratin 15, and semenogelin II. Means for preparing and characterizing antibodies are well known in the art (See, e.g., Antibodies: A Laboratory Manual, Cold Spring Harbor Laboratory, 1988; incorporated herein by reference).

Methods for generating polyclonal antibodies are well known in the art. Briefly, a polyclonal antibody is prepared by immunizing an animal with an immunogenic composition and collecting antisera from that immunized animal. A wide range of animal species may be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes may be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal may be bled and the serum isolated and stored, and/or the animal may be used to generate MAbs. For production of rabbit polyclonal antibodies, the animal may be bled through am ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol.

These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells may operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines may also be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane)prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3H$, $^{125}I$, $^{131}I$ $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99m}Tc$. Radioactively labeled monoclonal antibodies of the present invention are produced according to well-known methods in the art. For instance, monoclonal antibodies may be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

It will be appreciated by those of skill in the art that monoclonal or polyclonal antibodies specific for proteins that are preferentially expressed in metastatic or nonmetastatic human prostate cancer or prostate disease will have utilities in several types of applications. These may include the production of diagnostic kits for use in detecting or diagnosing human prostate disease. An alternative use would be to link such antibodies to therapeutic agents, such as chemotherapeutic agents, followed by administration to individuals with prostate disease, thereby selectively targeting the prostate disease cells for destruction. The skilled practitioner will realize that such uses are within the scope of the present invention.

D. Immunodetection Assays

1. Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature (Nakamura et al., 1987a; Nakamura et al., 1987b ).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a prostate disease-marker encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a prostate disease-specific antigen, such as a prostate or lymph node tissue section or specimen, a homogenized tissue extract, an isolated cell, a cell membrane preparation, a blood lymphocyte separated or purified forms of any of the above protein-containing compositions, or even any biological fluid that comes into contact with prostate tissues, including blood, lymphatic fluid, and even seminal fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. No. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as prostate cancer and benign prostate hyperplasia. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with prostate disease, the detection of reduced levels of an antigen encoded by a prostate disease marker nucleic acid, in comparison to the levels in a corresponding biological sample from a normal subject is indicative of a patient with prostate disease. The basis for such diagnostic methods lies, in part, with the finding that the nucleic acid prostate disease markers identified in the present invention are underexpressed in prostate cancer tissue samples or peripheral blood (see Examples below). By extension, it may be inferred that at least some of these markers produce lowered levels of encoded proteins, that may also be used as prostate disease markers.

Those of skill in the art are very familiar with differentiating between significantly lower expression of a biomarker, which represents a positive identification, and background expression of a biomarker. Indeed, background expression levels are often used to form a "cut-off" above which decreased staining will be scored as significant or positive. Significant expression may be represented by low levels of antigens in tissues or within body fluids, or alternatively, by a low proportion of cells from within a tissue that each give a positive signal.

2. Immunohistochemistry

The antibodies of the present invention may be used in conjunction with both fresh-frozen and formalin-fixed, paraffin-embedded tissue blocks prepared by immunohistochemistry(IHC). Any IHC method well known in the art may be used such as those described in *Diagnostic Immunopathology,* 2nd edition. edited by, Robert B. Colvin, Atul K. Bhan and Robert T. McCluskey. Raven Press, New York., 1995, (incorporated herein by reference) and in particular, Chapter 31 of that reference entitled Gynecological and Genitourinary Tumors (pages 579–597), by Debra A. Bell, Robert H. Young and Robert E. Scully and references therein.

3. ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of prostate disease marker proteins, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays(RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the prostate disease marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the prostate disease marker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labelled antibodies are added to the wells, allowed to bind to the prostate disease marker protein, and detected by means of their label. The amount of marker antigen in an unknown sample is then determined by mixing the sample with the labelled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate disease and/or clinical or biological sample to be tested under conditions effective to allow immunecomplex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention will be used to quantify and localize the expression of the encoded marker proteins. The antibody, for example, will be labeled by any one of a variety of methods and used to visualize the localized concentration of the cells producing the encoded protein.

The invention also relates to an in vivo method of imaging a pathological prostate condition using the above described monoclonal antibodies. Specifically, this method involves administering to a subject an imaging-effective amount of a detectably-labeled prostate disease-specific monoclonal antibody or fragment thereof and a pharmaceutically effective carrier and detecting the binding of the labeled monoclonal antibody to the diseased, or in the case of down regulated marker genes, healthy tissue. The term "in vivo imaging" refers to any method which permits the detection of a labeled monoclonal antibody of the present invention or fragment thereof that specifically binds to a diseased tissue located in the subject's body. A "subject" is a mammal, preferably a human. An "imaging effective amount" means that the amount of the detectably-labeled monoclonal antibody, or fragment thereof, administered is sufficient to enable detection of binding of the monoclonal antibody or fragment thereof to the diseased tissue, or the binding of the monoclonal antibody or fragment thereof in greater proportion to healthy tissue relative to diseased tissue.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriamepentaacetic acid (DTPA) and ethylene diaminetetracetic acid (EDTA). Examples of metallic ions suitable for use in this invention are $^{99m}Tc$, $^{123}I$, $^{131}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{210}Tl$.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration may also be intradermal or intracavitary, depending upon the body site under examination. After a sufficient time has lapsed, for example 30 minutes to 48 hours, for the monoclonal antibody or fragment thereof to bind with the target tissue, either diseased and/or healthy tissue, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue may be determined.

It will be apparent to those of skill in the art that a similar approach may be used to radio-image the production of the encoded prostate disease marker proteins in human patients. The present invention provides methods for the in vivo diagnosis of prostate disease in a patient. Such methods generally comprise administering to a patient an effective amount of a prostate disease specific antibody, which antibody is conjugated to a marker, such as a radioactive isotope or a spin-labeled molecule, that is detectable by non-invasive methods. The antibody-marker conjugate is allowed sufficient time to come into contact with reactive antigens that be present within the tissues of the patient, and the patient is then exposed to a detection device to identify the detectable marker.

5. Kits

In still further embodiments, the present invention concerns immunodetection kits for use with the immunodetection methods described above. As the encoded marker proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

E. Detection and Quantitation of RNA Species

One embodiment of the instant invention comprises a method for identification of prostate disease cells in a biological sample by amplifying and detecting nucleic acids corresponding to prostate disease cell markers. The biological sample may be any tissue or fluid in which prostate disease cells or peripheral blood cells might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to prostate disease-specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and prostate disease patients. In this way, it is possible to correlate the amount of marker detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared which are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. The most preferred methods of RT-PCR are as described in U.S. application Ser. No. 08/692,787, which is incorporated herein by reference in its entirety, and may be used in accordance with the present invention. In the later application, DNA free total cell RNA is primed with random hexamers and oligo dT and reverse transcribed to produce cDNA. The cDNAs from each reaction are normalized to the amplifiable β-actin cDNA content, and gene specific PCR amplification is performed on pools of normalized cDNA samples. The linear range of amplification of PCR products to empirically determined to allow quantitative comparison between amplified samples.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

Methods based on ligation of two (or more) oligonucleotides in the presence of nucleic acid having the sequence of the resulting "di-oligonucleotide", thereby amplifying the di-oligonucleotide, may also be used in the amplification step of the present invention (Wu et al., 1989).

3. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5. Other Assays

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay (RPA) was adapted for detection of single base mutations. In this type of RNase A mismatch cleavage assay, radiolabeled RNA probes transcribed in vitro from wild-type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

6. Kit Components

All the essential materials and reagents required for detecting prostate disease markers in a biological sample may be assembled together in a kit. The kit generally will comprise preselected primer pairs for one or more specific markers. For example a kit may include primers and/or probes for use in any molecular biology assay known to those of skill in the art, such as RT-PCR, in situ hybridization, Northern analysis and/or RPA, to detect RNA markers of normal tissue, BPH tissue, confined tumor tissue or metastically progressive tumor tissue, or any combination of these. Also included may be enzymes suitable for amplifying nucleic acids including various polymerases (RT, Taq, etc.), deoxynucleotides and buffers to provide the necessary reaction mixture for amplification. Preferred kits may also comprise primers for the detection of a control, non-differentially expressed RNA such as β-actin, for example.

The kits generally will comprise, in suitable means, distinct containers for each individual reagent and enzyme as well as for each marker primer pair. Preferred pairs of primers for amplifying nucleic acids are selected to amplify the sequences designated herein as SEQ ID NO:1, SEQ ID NO:2, SEQ ID NO:3 or SEQ ID NO:14.

In certain embodiments, kits will comprise hybridization probes specific for differentially expressed markers. The probes are designed to hybridize to a sequence or a complement of a sequence designated herein as SEQ ID NO:1, SEQ ID NO:2, SEQ ID NO:3 or SEQ ID NO:14. Such kits generally will comprise, in suitable means for close confinement, distinct containers for each individual reagent and enzyme as well as for each marker hybridization probe.

F. Pharmaceutical Compositions

As stated above, evidence suggests a role for prostate-specific transglutaminase, cytokeratin 15, and semenogelin II in prostate cancers. The present invention involves a cell-based assay technique for identifying and evaluating chemical compounds and agents which affect the production of prostate-specific transglutaminase, cytokeratin 15, and/or semenogelin II, thereby identifying chemotherapeutic compounds for use in the treatment of prostate cancer. This cell-based assay also is believed to work equally well in assessing compounds for their stimulation of prostate-specific transglutaminase, cytokeratin 15, and/or semenogelin II production in prostate cancers.

Specifically, cells are transfected with an expression vector comprising a DNA sequence encoding a promoter region of prostate-specific transglutaminase, cytokeratin 15, and/or semenogelin II operatively linked to a reporter gene encoding an assayable product. The cells are then cultured under conditions which permit expression of the assayable product. The prostate-specific transglutaminase, cytokeratin 15, and/or semenogelin II promoter region is preferably cloned from genomic DNA but may be synthesized de novo.

After transfection with the expression vector, the cells are incubated with at least one compound suspected of possessing regulatory activity for prostate-specific transglutaminase, cytokeratin 15, and/or semenogelin II expression. Chemical agents and factors can be identified by their ability to modulate the expression of the reporter gene and thereby increase or decrease the production of the assayable product. Such chemical compounds are selected from small chemical libraries, peptide libraries, and/or collections of natural products.

The present invention is distinguished from other techniques for identifying chemical compounds, as it specifically identifies chemical compounds, agents, factors and other substances which affect prostate-specific transglutaminase, cytokeratin 15, and/or semenogelin II production by cells. These agents are identified by their capacity to affect the activity of prostate-specific transglutaminase, cytokeratin 15, and/or semenogelin II promoters. Decrease in activity of the promoters is measured by a correspondent decrease in production of the reporter gene's product. Increase in activity of the promoters is measured by a correspondent increase in production of the reporter gene's product. Thus, decrease in the production of, for example, firefly luciferase under the control of a prostate-specific transglutaminase, cytokeratin 15, and/or semenogelin II promoter, indicates that prostate-specific transglutaminase, cytokeratin 15, and/or semenogelin II promoter activity is being suppressed by the compound being tested; an increase in the production of firefly luciferase in indicative of stimulation of the prostate-specific transglutaminase, cytokeratin 15, and/or semenogelin II promoter. The affect in production of the assaying product reflects the affect in prostate-specific transglutaminase, cytokeratin 15, and/or semenogelin II that would occur in a cell treated with the compound.

Ultimately, when cancer patients are treated with chemical compounds shown to increase prostate-specific transglutaminase, cytokeratin 15, and/or semenogelin II promoter activity, prostate-specific transglutaminase, cytokeratin 15, and/or semenogelin II production by tumor and/or peripheral blood cells will be stimulated. Therefore, compounds identified by this assay technique that increase prostate-specific transglutaminase, cytokeratin 15, and semenogelin II promoter activity can be used in the treatment of prostate cancers which metastasize and other conditions where a reduction in prostate-specific transglutaminase, cytokeratin 15, and/or semenogelin II production is produced and results in detrimental effects.

1. Prostate Disease Marker Gene Promoters

A technique often employed by those skilled in the art of protein production today is to obtain a "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved, for purposes of the present invention, by cloning of a genomic DNA molecule containing a prostate-specific transglutaminase, cytokeratin 15, and/or semenogelin II promoter. Alternatively, having knowledge of the prostate-specific transglutaminase, cytokeratin 15, and/or semenogelin II promoter sequence, the promoter may be synthesized according to standard techniques.

The first step in a cloning procedure is the screening of an appropriate DNA library, such as, in the present case, a tumor-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature. Nucleotide sequences in accordance with SEQ ID NO:1, SEQ ID NO:2, SEQ ID NO:3, and/or SEQ ID NO:14 may be used as probes or in the generation of antibodies, as described in the preceding sections, to screening protocols. Additionally, a 4409 bp fragment of the semenogelin II promoter region is set forth in nucleotides 1 to 4409 of SEQ ID NO:14.

2. Reporter Genes

A reporter gene is a gene which produces a product having a readily identifiable and assayable phenotype. One skilled in the art will however recognize other useful reporter genes which will work equally well in the present invention. Examples of such reporter genes include, but are not limited to, firefly luciferase (Promega, Madison, Wis.), chloramphenicol acetyl transferase (Promega), β-galactosidase (Promega), green fluorescent protein (Clontech, Palo Alto, Calif.), human growth hormone (Amersham Life Science, Arlington Heights, Ill.), alkaline phosphatase (Clontech) and β-glucuronidase (Clontech).

3. Expression Constructs

The expression constructs, commonly referred to as vectors, that can be utilized in the disclosed cell-based assay of the instant invention may vary considerably. The vectors may be "standard" expression vectors, i.e., plasmids that contain one or more effector genes and regulatory elements required for expression of the effector gene in cells. Plasmid expression vectors include any plasmid, cosmid or phage construct that is capable of supporting expression of encoded genes in mammalian cells, such as pUC or Bluescript™ plasmid series. Alternatively, these vectors may be more complex, such as the viral vectors discussed below.

The regulatory elements of an expression vector will comprise at least a promoter, in this case the prostate-specific transglutaminase, cytokeratin 15, and/or semenogelin II promoter and a reporter gene (as discussed above), and also may include structures that assist in replication, such as origins of replication. In addition, almost all expression vectors contain multipurpose cloning regions that have numerous restriction enzyme sites. One also typically will include a polyadenylation signal to effect proper polyadenylation of the transcript. The nature of the polyadenylation signal is not believed to be crucial to the successful practice of the invention, and any such sequence may be employed. Examples include SV40 and bovine growth hormone poly-A sites. Also contemplated as an element of the expression construct is a terminator. These elements can serve to enhance message levels and to minimize read through from the construct into other sequences. Finally, expression vectors typically have selectable markers, often in the form of antibiotic resistance genes, that permit selection of cells that carry these vectors.

As stated above, in certain embodiments of the present invention, the expression construct comprises a virus or engineered construct derived from a viral genome. The ability of certain viruses to enter cells via receptor-mediated endocytosis, and, in some cases, integrate into the host cell chromosomes, have made them attractive candidates for gene transfer in to mammalian cells.

a. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pot, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a prostate-specific transglutaminase, cytokeratin 15, and/or semenogelin II promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell typos. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

b. Adenoviruses

Human adenoviruses are double-stranded DNA tumor viruses with genome sizes of approximate 36 kB (Tooze, 1981). As a model system for eukaryotic gene expression, adenoviruses have been widely studied and well characterized, which makes them an attractive system for development of adenovirus as a gene transfer system. This group of viruses is easy to grow and manipulate, and exhibit a broad host range in vitro and in vivo. In lytically infected cells, adenoviruses are capable of shutting of host protein synthesis, directing cellular machinery to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans. The characteristics of adenoviruses rendered them good candidates for use in gene transfer both in, vitro and in vivo (Grunhaus and Horwitz, 1992).

Particular advantages of an adenovirus system for delivering foreign proteins to a cell include the ability to substitute relatively large pieces of viral DNA by foreign DNA, the structural stability of recombinant adenoviruses, the safety of adenoviral administration to humans, and lack of any known association of adenoviral infection with cancer or malignancies, the ability to obtain high titers of the recombinant virus, and the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus and Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Persistent expression of transgenes following adenoviral infection has also been reported.

c. Other Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viruses offer several attractive features for gene transfer into various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for gene transfer into liver cells. Chang et al. recently introduced the chloramphenicol acetyltransferase (CAT) gene into duck hepatitis B virus, genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

d. Alternative Delivery Systems

In order to effect expression of reporter gene constructs, the expression vector must be delivered into a cell. As described above, one mechanism for delivery is via viral infection where the expression vector is encapsidated in an infectious adenovirus particle.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley and Kaplan, 1979) and lipofectamine-DNA complexes, cell sonication (Fechheimer et al., 1987), gene bombardment using high velocity microprojectiles (Yang et al, 1990), polycations (Boussif et al., 1995) and receptor-mediated transfection (Wu and Wu, 1987; Wu and Wu, 1988).

In one embodiment of the invention, the expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$-precipitited plasmids results in expression of the transfected genes. It is envisioned that DNA encoding a construct according to the present invention may also be transferred in a similar manner.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery to cells that exhibit upregulation of EGF receptor, such as tumor cells. Galactose can be used to target the asialoglycoprotein receptor on liver cells. Also, antibodies to CD5 (CLL), CD22 (lymphoma), CD25 (T-cell leukemia) and MAA (melanoma) can similarly be used as targeting moieties.

G. Therapeutics

The role which prostate specific transglutaminase, cytokeratin 15, and semenogelin II play in the etiology of metastatic prostate cancer is not yet completely understood. However, upon confirmation of the active role of prostate specific transglutaminase, cytokeratin 15, and/or semenogelin II in prostate diseases, the present invention will provide metastatic prostate cancer therapy by provision of the appropriate wild-type gene. In these aspects of the present invention, prostate specific transglutaminase, cytokeratin 15, and/or semenogelin II are provided to an animal with a prostate disease, in the same manner that other disease suppressors are provided, following identification of a cell type that lacks prostate specific transglutaminase, cytokeratin 15, and/or semenogelin II or that has an aberrant prostate specific transglutaminase, cytokeratin 15, and/or semenogelin II.

In alternative aspects, where the levels or activity of prostate specific transglutaminase, cytokeratin 15, and/or semenogelin II is too high, then inhibition of prostate specific transglutaminase, cytokeratin 15, and/or semenogelin II, or the genes encoding prostate specific transglutaminase, cytokeratin 15, and/or semenogelin II would be adopted as a therapeutic strategy. Inhibitors would be any molecule that reduces the activity or amounts of prostate specific transglutaminase, cytokeratin 15, and/or semenogelin II, or a gene encoding prostate specific transglutaminase, cytokeratin 15, and/or semenogelin II, including antisense, ribozymes and the like, as well as small molecule inhibitors.

1. Gene Therapy

The general approach to the aspects of the present invention concerning metastatic prostate cancer therapeutics is to provide a cell with a prostate specific transglutaminase, cytokeratin 15, and/or semenogelin II protein, thereby permitting the proper regulatory activity of the proteins to take effect. While it is conceivable that the protein may be delivered directly, a preferred embodiment involves providing a nucleic acid encoding a prostate specific transglutaminase, cytokeratin 15, and/or semenogelin II protein to the cell. Following this provision, the polypeptide is synthesized by the transcriptional and translational machinery of the cell, as well as any that may be provided by the expression construct. In providing antisense, ribozymes and other inhibitors, the preferred mode is also to provide a nucleic acid encoding the construct to the cell. All such approaches are herein encompassed within the term "gene therapy".

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

a. DNA Delivery Using Viral Vectors

The ability of certain viruses to infect cells or enter cells via receptor-mediated endocytosis, and to integrate into host cell genome and express viral genes stably and efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

i. Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue-specific transforming construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 19783), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E-1 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1991; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993). Recombinant adenovirus and adeno-associated virus (see below) can both infect and transduce non-dividing human primary cells.

ii. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1985; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

iii. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

iv. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new, insight was gained into the structure-function relationship of different viral sequences. In vitro studies showed that the virus could retain the ability for helper-dependent packaging and reverse transcription despite the deletion of up to 80% of its genome (Norwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

v. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

b. Other Methods of DNA Delivery

In various embodiments of the invention, DNA is delivered to a cell as an expression construct. In order to effect expression of a gene construct, tie expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane. Some of these techniques may be successfully adapted for in vivo or ex vivo use, as discussed below.

i. Liposome and Nanocapsule-Mediated Transfection

In a further embodiment of the invention, the expression construct may be entrapped in a liposome. In certain embodiments, the use of liposomes and/or nanoparticles is contemplated for the introduction of prostate specific transglutaminase, cytokeratin 15, and/or semenogelin II protein, peptides or agents, stimulators, inhibitors, or gene therapy vectors, including both wild-type and antisense vectors, into host cells. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Nanocapsules can generally entrap compounds in a stable and reproducible way. To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

ii. Electroporation

In certain embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii Calcium Phosphate Precipitation

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1 990).

iv. DEAE-Dextran Treatment

In another embodiment, the expression construct is delivered into the cell using DEAE-dextran followed by polyethylene glycol. In this manner, reporter plasmids were introduced into mouse myeloma and erythroleukemia cells (Gopal, 1985).

v. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

vi. Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK- fibroblasts have been transacted with the thymidine kinase gene by sonication loading (Fechheimer et al., 1987).

vii. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

viii. Receptor Mediated Transfection

Still further expression constructs that may be employed to deliver the tissue-specific promoter and transforming construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In the context of the present invention, the ligand will be chosen to correspond to a receptor specifically expressed on the neuroendocrine target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

2. Antisense

In the alternative embodiments discussed above, the prostate specific transglutaminase, cytokeratin 15, and/or semenogelin II nucleic acids employed may actually encode antisense constructs that hybridize, under intracellular conditions, to prostate specific transglutaminase, cytokeratin 15, and/or semenogelin II nucleic acids. The term "antisense construct" is intended to refer to nucleic acids, preferably oligonucleotides, that are complementary to the base sequences of a target DNA or RNA. Targeting double-stranded (ds) DNA with an antisense construct leads to triple-helix formation; targeting RNA will lead to double-helix formation. Antisense nucleic acids, when introduced into a target cell, specifically bind to their target polynucleotide, for example prostate specific transglutaminase, cytokeratin 15, and/or semenogelin II, and interfere with transcription, RNA processing, transport, translation and/or stability. Antisense RNA constructs, or DNA encoding such antisense RNAs, may be, employed to inhibit prostate specific transglutaminase, cytokeratin 15, and/or semenogelin II gene transcription or translation or both within the cells of the present invention.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the term "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the prostate specific transglutaminase, cytokeratin 15, and/or semenogelin II gene sequences may be employed in the context of antisense construction, short oligonucleotides are easier to make and increase in vivo accessibility. However, both binding affinity and sequence specificity of an antisense oligonucleotide to its complementary target increases with increasing length. One can readily determine whether a given antisense nucleic acid is effective at targeting of the corresponding host cell gene simply by testing the constructs in vitro to determine whether the function of the endogenous gene is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression.

3. Ribozymes

Another method for inhibiting prostate specific transglutaminase, cytokeratin 15, and/or semenogelin II expression contemplated in the present invention is via ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozyme can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Several different ribozyme motifs have been described with RNA cleavage activity (Symons, 1992). Examples that are expected to function equivalently for the down regulation of prostate specific transglutaminase, cytokeratin 15, and/or semenogelin II include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

The large number of possible cleavage sites in prostate specific transglutaminase, cytokeratin 15, and semenogelin II coupled with the growing number of sequences with demonstrated catalytic RNA cleavage activity indicates that a large number of ribozymes that have the potential to downregulate prostate specific transglutaminase, cytokeratin 15, and semenogelin II are available. Additionally, due to the sequence variation among the prostate specific transglutaminase, cytokeratin 15, and semenogelin II, ribozymes could be designed to specifically cleave prostate specific transglutaminase, cytokeratin 15, or semenogelin II. Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in prostate specific transglutaminase, cytokeratin 15, and semenogelin II-targeted ribozymes is simply a matter of preparing and testing a given sequence, and is a routinely practiced "screening" method known to those of skill in the art.

4. Homologous Recombination

Although genetic transformation tends to be quite efficient, it is also accompanied by problems associated with random insertion. Random integration can lead to the inactivation of essential genes, or to the aberrant expression of the introduced gene. Additional problems associated with genetic transformation include mosaicism due to multiple integrations, and technical difficulties associated with generation of replication defective recombinant viral vectors.

Some of these drawbacks can be overcome by the utilization of a technique known as homologous recombination (Koller and Smithies, 1992). This technique allows the precise modification of existing genes, overcomes the problems of positional effects and insertional inactivation, and allows the inactivation of specific genes, as well as the replacement of one gene for another. Methods for homologous recombination are described in U.S. Pat. 5,614,396, incorporated herein in its entirety by reference.

Thus a preferred method for the delivery of transgenic constructs involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, thus permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. Thus, another approach for inhibiting prostate specific transglutaminase, cytokeratin 15, and semenogelin II involves the use of homologous recombination, or "knock-out technology". This is accomplished by including a mutated or vastly deleted form of the heterologous gene between the flanking regions within the construct. The arrangement of a construct to effect homologous recombination might be as follows:

. . . vector.5'-flanking sequence-selected gene. selectable marker gene.flanking sequence-3'.vector . . .

Thus, using this kind of construct, it is possible, in a single recombinatorial event, to (i) "knock out" an endogenous gene, (ii) provide a selectable marker for identifying such an event and (iii) introduce a transgene for expression.

Another refinement of the homologous recombination approach involves the use of a "negative" selectable marker. One example of the use of the cytosine deaminase gene in a negative selection method is described in U.S. Pat. No. 5,624,830. The negative selection marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

5. Marker genes

In certain aspects of the present invention, specific cells are tagged with specific genetic markers to provide information about the fate of the tagged cells. Therefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

a. Screening

Exemplary enzymes include esterases, phosphatases, proteases (tissue plasminogen activator or urokinase) and other enzymes capable of being detected by their activity, as will be known to those skilled in the art. Contemplated for use din the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other particular examples are the enzyme chloramphenicol acetyltransferase (CAT) which may be employed with a radiolabeled substrate, firefly and bacterial luciferase, and the bacterial enzymes β-galactosidase and β-glucuronidase. Other marker genes within this class are well known to those of skill in the art, and are suitable for use in the present invention.

b. Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

6. Excision of Transgenes

In certain embodiments of the present invention, rescue of a prostate specific transglutaminase, cytokeratin 15, and/or semenogelin II gene or genetic construct is desired. The present invention contemplates the use of site-specific recombination systems to rescue specific genes out of a genome, and to excise specific transgenic constructs from the genome.

Members of the integrase family are proteins that bind to a DNA recognition sequence, and are involved in DNA recognition, synapsis, cleavage, strand exchange, and religation. Currently, the family of integrases includes 28 proteins from bacteria, phage, and yeast which have a common invariant His-Arg-Tyr triad (Abremski and Hoess, 1992). Four of the most widely used site-specific recombination systems for eukaryotic applications include: Cre-loxP from bacteriophage P1 (Austin et al., 1981); FLP-FRT from the 2μ plasmid of *Saccharomyces cerevisiae* (Andrews et al., 1985),; R-RS from *Zygosaccharomyces rouxii* (Maeser and Kahmann, 1991) and gin-gix from bacteriophage Mu (Onouchi et al., 1995). The Cre-loxP and FLP-FRT systems have been developed to a greater extent than the latter two systems. The R-RS system, like the Cre-loxP and FLP-FRT systems, requires only the protein and its recognition site. The Gin recombinase selectively mediates DNA inversion between two inversely oriented recombination sites (gix) and requires the assistance of three additional factors: negative supercoiling, an enhancer sequence and its binding protein Fis.

The present invention contemplates the use of the Cre/Lox site-specific recombination system (Sauer, 1993, available through Gibco/BRL, Inc., Gaithersburg, Md.) to rescue specific genes out of a genome, and to excise specific transgenic constructs from the genome. The Cre (causes recombination)-lox P (locus of crossing-over(x)) recombination system, isolated from bacteriophage P1, requires only the Cre enzyme and its loxP recognition site on both partner molecules (Sternberg and Hamilton, 1981). The loxP site consists of two symmetrical 13 bp protein binding regions separated by an 8 bp spacer region, which is recognized by the Cre recombinase, a 35 kDa protein. Nucleic acid sequences for loxP (Hoess et al., 1982) and Cre (Sternberg et al., 1986) are known. If the two lox P sites are cis to each other, an excision reaction occurs; however, if the two sites are trans to one another, an integration event occurs. The Cre protein catalyzes a site-specific recombination event. This event is bidirectional, i.e., Cre will catalyze the insertion of sequences at a LoxP site or excise sequences that lie between two LoxP sites. Thus, if a construct for insertion also has flanking LoxP sites, introduction of the Cre protein, or a polynucleotide encoding the Cre protein, into the cell will catalyze the removal of the construct DNA. This technology is enabled in U.S. Pat. No. 4,959,317, which is hereby incorporated by reference in its entirety.

An initial in vivo study in bacteria showed that the Cre excises loxP-flanked DNA extrachromosomally in cells expressing the recombinase (Abremski et al., 1988). A major question regarding this system was whether site-specific recombination in eukaryotes could be promoted by a bacterial protein. However, Sauer (1987) showed that the system excises DNA in *S. cerevisiae* with the same level of efficiency as in bacteria.

Further studies with the Cre-loxP system, in particular the ES cells system in mice, has demonstrated the usefulness of the excision reaction for the generation of unique transgenic animals. Homologous recombination followed by Cre-mediated deletion of a loxP-flanked neo-tk cassette was used to introduce mutations into ES cells. This strategy was repeated for a total of 4 rounds in the same line to alter both alleles of the rep-3 and mMsh2 loci, genes involved in DNA mismatch repair (Abuin and Bradley, 1996). Similarly, a transgene which consists of the 35S promoter/luciferase gene/loxP/35S promoter/hpt gene/loxP ($luc^+hyg^+$) was introduced into tobacco. Subsequent treatment with Cre causes the deletion of the hyg gene ($luc^+hyg^S$) at 50% efficiency (Dale and Ow, 1991). Transgenic mice which have the Ig light chain κ constant region targeted with a loxP-flanked neo gene were bred to Cre-producing mice to remove the selectable marker from the early embryo (Lakso et al., 1996). This general approach for removal of markers stems from issues raised by regulatory groups and consumers concerned about the introduction of new genes into a population.

An analogous system contemplated for use in the present invention is the FLP/FRT system. This system was used to target the histone 4 gene in mouse ES cells with a FRT-flanked neo cassette followed by deletion of the marker by FLP-mediated recombination. The FLP protein could be obtained from an inducible promoter driving the FLP or by using the protein itself (Wigley et al., 1994).

The present invention also contemplates the use of recombination activating genes (RAG) 1 and 2 to excise specific transgenic constructs from the genome, as well as to rescue specific genes from the genome. RAG-1 (GenBank accession number M29475) and RAG-2 (GenBank accession numbers M64796 and M33828) recognize specific recombination signal sequences (RSSs) and catalyze V(D)J recombination required for the assembly of immunoglobulin and T cell receptor genes (Schatz et al., 1989; Oettinger et al., 1990; Cumo and Oettinger, 1994). Transgenic expression of RAG-1 and RAG-2 proteins in non-lymphoid cells supports V(D)J recombination of reporter substrates (Oettinger et al., 1990). For use in the present invention, the transforming construct of interest is engineered to contain flanking RSSs. Following transformation, the transforming construct that is internal to the RSSs can be deleted from the genome by the transient expression of RAG-1 and RAG-2 in the transformed cell.

H. Pharmaceutical Compositions

1. Pharmaceutically Acceptable Carriers

In another embodiment of the present invention, there are provided methods for the treatment of cancer. The present invention contemplates the use of compounds having stimulatory activity to increase expression from the prostate-specific transglutaminase, cytokeratin 15, and/or semenogelin II promoters and, hence, to counteract the down expression of prostate-specific transglutaminase, cytokeratin 15, and/or semenogelin II in prostate tissue cells or peripheral blood cells seen in metastatic disease. Treatment methods will involve treating an individual with an effective amount of a prostate-specific transglutaminase, cytokeratin 15, and/or semenogelin II stimulatory compound. An effective amount is described, generally, as that amount sufficient to detectably and repeatedly increase the level of prostate-specific transglutaminase, cytokeratin 15, and/or semenogelin II in a cell.

Aqueous compositions of the present invention comprise an effective amount of the prostate specific transglutaminase, cytokeratin 15, and/or semenogelin II protein, peptide, epitopic core region, stimulator, inhibitor, and the like, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

Administration of the compound to a patient will follow general protocols for the administration of chemotherapeutics, taking into account the toxicity, if any, of the compound. It is anticipated that the treatment cycles would be repeated as necessary.

Aqueous compositions of the present invention comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a prostate specific transglutaminase, cytokeratin 15, and/or semenogelin II agent as an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A prostate specific transglutaminase, cytokeratin 15, and/or semenogelin II protein, peptide, agonist or antagonist of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580).

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active prostate specific transglutaminase, cytokeratin 15, and/or semenogelin II protein-derived peptides or agents may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

2. Combination Therapies

Therapies according to the present invention encompass combination therapies that include treatment with pro-prostate-specific transglutaminase, cytokeratin 15, and/or semenogelin II compositions as well as standard chemo- and radiotherapies. For example, chemotherapeutics include, but are not limited to, cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate. Also included in combined therapies may be x- and γ-irradiation.

EXAMPLES

Example 1

Identification of Prostate Markers by Use of Southern Differential Hybridization Prostate enriched cDNAs were purchased from Clontech. The cDNAs were PCR amplified using adapter primers attached to both ends of the cDNAs. The amplified cDNAs were cloned into pGEM-T plasmid vector (Promega) by T-A cloning, and transformation to generate a cDNA library. Transformed cells were plated and a total of 200 colonies were randomly picked from the prostate enriched cDNA library. The cDNA inserts were amplified by PCR from the plasmid templates using T7 and SP6 primers. β-Actin and PSA inserts were also prepared as controls. The inserts were run on duplicate 2% agarose gels and blotted onto nylon membranes. $^{32}$P labeled cDNA probes were prepared, separately, from normal prostate RNA and pools of RNAs from 11 other tissues (liver, pancreas, testis, thymus, brain, mammary gland, skeletal muscle, kidney, lung, small intestine and spleen). The two membranes (each have identical amounts of cDNA from individual clones) were hybridized with the two probes (normal prostate or pool of other tissues) separately. Clones that hybridized only to the prostate cDNA probe were identified as potential prostate specific genes.

Example 2

Northern Analysis of Prostate Markers

Northern analysis was performed to confirm that the genes were expressed specifically in prostate tissue. Total cell RNA was isolated from human tissue samples, and Northern blots prepared (according to Sambrook et al., 1989). The cDNA clones that were identified as potential prostate specific genes were $^{32}$P labeled as probes, and hybridized against the Northern blots. UC Clone #51 (prostate-specific transglutaminase) message is preferentially expressed in prostate tissue relative to spleen, thymus, testis, ovary, small intestine, colon, and peripheral blood. UC Clone #57 (semenogelin II) message is preferentially expressed in normal prostate tissue when compared to the lack of detectable expression in samples taken from spleen, thymus, testis, ovary, small intestine, colon, and peripheral blood.

Example 3

DNA Sequences of Prostate Markers

The nucleotide sequences of prostate expressed clones were determined by dideoxy termination sequencing using either the ABI or Pharmacia automated sequencers. The DNA sequence of UC Clone #51 (SEQ ID NO:1) is identical in sequence to the sequence of prostate-specific transglutaminase (GenBank Accession #s L34840, I20492). The DNA sequence of Clone #56 (SEQ ID NO:2) is identical in sequence to the sequence of cytokeratin 15 (GenBank Accession #X07696). A third prostate specific gene, UC Clone #57 (SEQ ID NO:3) is identical in sequence to the sequence of semenogelin II (GenBank Accession #M81652). The identified sequences are provided in Table 2.

TABLE 2

DNA Sequences of Prostate Markers

UC Clone #51 (SEQ ID NO:1) prostate-specific transglutaminase, GenBank Accession #s L34840, I20492

```
5'AATTCTAAAAATGCTTTTGCAAGCTTGCATGCCTGCAGGTGCAGCGGCCGCC
AGTGTGATGGATATCTGCAGAATTCGGCTTGCGCTCAGCTGGAATTCCGCAG
AGATAGAGTCTTCCCTGGCATTGCAGGAGAGAATCTGAAGGGATGATGGATG
CATCAAAAGAGCTGCAAGTTCTCCACATTGACTTCTTGAATCAGGACAACGC
CGTTTCTCACCACACATGGGAGTTCCAAACGAGCAGTCCTGTGTTCCGGCGA
GGACAGGTGTTTCACCTGCGGCTGGTGCTGAACCAGCCCCTACAATCCTACC
ACCAACTGAAACTGGAATTCAGCACAGGGCCGAATCCTAGCATCGCCAAACA
CACCCTGGTGGTGCTCGACCCGAGGACGCCCTCAGACCACTACAACTGGCAG
GCAACCCTTCAAAATGAGTCTGGCAAAGAGGTCACAGTGGCTGTCACCAGTT
CCCCCAATGCCATCCTGGGCAAGTACCAACTAAACGTGAAAACTGGAAACCA
CATCCTTAAGTCTGAAGAAAACATCCTATACCTTCTCTTCAACCCATGGTGTA
AAGAGGACATGGTTTTCATGCCTGATGAGGACGAGCGCAAAGAGTACATCCT
CAATGACACGGGCTGCCATTACGTGGGGGCTGCCAGAAGTATCAAATGCAAA
CCCTGGAACTTTGGTCAGTTTGAGAAAAATGTCCTGGACTGCTGCATTTCCCT
GCTGACTGAGAGCTCCCTCAAGCCCACAGATAGGAGGGACCCCGTGCTGGTG
TGCAGGGCCATGTGTGCTATGATGAGCTTTGAGAAAGGCCAGGGCGTGCTCA
TTGGGAATTGGACTGGGGACTACGAAGGTGGCACAGCCCCATACAAGTGGAC
AGGCAGTGCCCCGATCCTGCAGCAGTACTACAACACGAAGCAGGCTGTGTGC
TTTGGCCAGTGCTGGGTGTTTGCTGGGATCCTGACTACAGTGCTGAGAGCGTT
GGGCATCCCAGCACGCAGTGTGACAGGCTTCGATTCAGCTCACGACACAGAA
AGGAACCTCACGGTGGACACCTATGTGAATGAGAATGGCGAGAAAATCACC
AGTATGACCCACGACTCTGTCTGGAATTTCCATGTGTGGACGGATGCCTGGAT
GAAGCGACCCTACGACGGCTGGCAGGCTGTGGACGCAACGCCGCAGGAGCG
AAGCCAGGGTGTCTTCTGCTGTGGGCCATCACCACTGACCGCCATCCGCAAA
GGTGACATCTTTATTGTCTATGACACCAGATTCGTCTTCTCAGAAGTGAATGG
TGACAGGCTCATCTGGTTGGTGAAGATGGTGAATGGGCAGGAGGAGTTACAC
GTAATTTCAATGGAGACCACAAGCATCGGGAAAAACATCAGCACCAAGGCA
GTGGGCCAAGACAGGCGGAGAGATATCACCTATGAGTACAAGTATCCAGAA
GGCTCCTCTGAGGAGAGGCAGGTCATGGATCATGCCTTCCTCCITCTCAGTTC
TGAGAGGGAGCACAGACAGCCTGTAAAAGAGAACTTTCTTCACATGTCGGTA
CAATCAGATGATGTGCTGCTGGGAAACTCTGTTAATTTCACCGTGATTCTTAA
AAGGAAGACCGCTGCCCTACAGAATGTCAACATCTTGGGCTCCTTTGAACTA
CAGTTGTACACTGGCAAGAAGATGGCAAAACTGTGTGACCTCAATAAGACCT
CGCAGATCCAAGGTCAAGTATCAGAAGTGACTCTGACCTTGGACTCCAAGAC
CTACATCAACAGCCTGGCTATATTAGATGATGAGCCAGTTATCAGAGGTTTCA
TCATTGCGGAAATTGTGGAGTCTAAGGAAATCATGGCCTCTGAAGTATTCAC
GTCAAACCAGTACCCTGAGTTCTCTATAGAGTTGCCTAACACAGGCAGAATT
GGCCAGCTACTTGTCTGCAATTGTATCTTCAAGAATACCCTGGCCATCCCTTT
GACTGACGTCAAGTTCTCTTTGGAAAGCCTGGGCATCTCCTCACTACAGACCT
CTGACCATGGGACGGTGCAGCCTGGTGAGACCATCCAATCCCAAATAAAATG
CACCCCAATAAAAACTGGCCCAAGAAATTTATCGTCAAGTTAAGTTCCAAA
CAAGTGAAAGAGATTAATGCTCAGAAGATTGTTCTCATCACCAAGTAGCCTT
GTCTGATGCTGTGGAGCCTTAGTTGAGATTTCAGCATTTCCTACCTTGTGCTT
AGCTTTCAGATTATGGATGATTAAATTTGATGACTTATATGAGGGCAGATTCA
```

TABLE 2-continued

DNA Sequences of Prostate Markers

AGAGCCAGCAGGTCAAAAAGGCCAACACAACCATAAGCAGCCAGACCCACA
AGGCCAGGTCCTGTGCTATCACAGGGTCACCTCTTTTACAGTTAGAAACACCA
GCCGAGGCCACAGAATCCCATCCCTTTCCTGAGTCATGGCCTCAAAAATCAG
GGCCACCATTGTCTCAATTCAAATCCATAGATTTCGAAGCCACAGAGCTCTTC
CCTGGAGCAGCAGACTATGGGCAGCCCAGTGCTGCCACCTGCTGACGACCCT
TGAGAAGCTGCCATATCTTCAGGCCATGGGTTCACCAGCCCTGAAGGCACCT
GTCAACTGGAGTGCTCTCTCAGCACTGGGATGGGCCTGATAGAAGTGCATTC
TCCTCCTATTGCCTCCATTCTCCTCTCTATCCCTGAAATCCAGGAAGTCCCT
CTCCTGGTGCTCCAAGCAGTTTGAAGCCCAATCTGCAAGGACATTTCTCAAGG
GCCATGTGGTTTTGCAGACAACCCTGTCCTCAGGCCTGAACTCACCATAGAG
ACCCATGTCAGCAAACGGTGACCAGCAAATCCTCTTCCCTTATTCTAAAGCTG
CCCCTTGGGAGACTCCAGGGAGAAGGCATTGCTTCCTCCCTGGTGTGAACTCT
TTCTTTGGTATTCCATCCACTATCCTGGCAACTCAAGGCTGCTTCTGTTAACTG
AAGCCTGCTCCTTCTTGTTCTGCCCTCCAGAGATTTGCTCAAATGATCAATAA
GCTTTAAATTAAACCGGAATCCGCGGAATTC-3'
UC Clone #56 (SEQ ID NO:2) cytokeratin 15,
GenBank Accession #X07696

5'GGTACCTCCTGCCAGCACCTCTTGGGTTTGCTGAGAACTCACGGGCTCCAGC
TACCTGGCCATGACCACCACATTTCTGCAAACTTCTTCCTCCACCTTTGGGGG
TGGCTCAACCCGAGGGGGTTCCCTCCTGGCTGGGGGAGGTGGCTTTGGTGGG
GGGAGTCTCTCTGGGGGAGGTGGAAGCCGAAGTATCTCAGCTTCTTCTGCTA
GGTTTGTCTCTTCAGGGTCAGGAGGAGGATATGGGGGTGGCATGAGGGTCTG
TGGCTTTGGTGGAGGGGCTGGTAGTGTTTTCGGTGGAGGCTTTGGAGGGGGC
GTTGGTGGGGGTTTTGGTGGTGGCTTTGGTGGTGGCGATGGTGGTCTCCTCTC
TGGCAATGAGAAAATTACCATGCAGAACCTCAATGACCGCCTGGCCTCCTAC
CTGGACAAGGTACGTGCCCTGGAGGAGGCCAATGCTGACCTGGAGGTGAAG
ATCCATGACTGGTACCAGAAGCAGACCCCAGCCAGCCCAGAATGCGACTACA
GCCAATACTTCAAGACCATTGAAGAGCTCCGGGACAAGATCATGGCCACCAC
CATCGACAACTCCCGGGTCATCCTGGAGATCGACAATGCCAGGCTGGCTGCG
GACGACTTCAGGCTCAAGTATGAGAATGAGCTGGCCCTGCGCCAGGGCGTTG
AGGCTGACATCAACGGCTTGCGCCGAGTCCTGGATGAGCTGACCCTGGCCAG
GACTGACCTGGAGATGCAGATCGAGGGCCTGAATGAGGAGCTAGCCTACCTG
AAGAAGAACCACGAAGAGGAGATGAAGGAGTTCAGCAGCCAGCTGGCCGGC
CAGGTCAATGTGGAGATGGACGCAGCACCGGGTGTGGACCTGACCCGTGTGC
TGGCAGAGATGAGGGAGCAGTACGAGGCCATGGCGGAGAAGAACCGCCGGG
ATGTCGAGGCCTGGTTCTTCAGCAAGACTGAGGAGCTGAACAAAGAGGTGGC
CTCCAACACAGAAATGATCCAGACCAGCAAGACGGAGATCACAGACCTGAG
ACGCACGATGCAGGAGCTGGAGATCGAGCTGCAGTCCCAGCTCAGCATGAAA
GCTGGGCTGGAGAACTCACTGGCCGAGACAGAGTGCCGCTATGCCACGCAGC
TGCAGCAGATCCAGGGGCTCATTGGTGGCCTGGAGGCCCAGCTGAGTGAGCT
CCGATGCGAGATGGAGGCTCAGAACCAGGAGTACAAGATGCTGCTTGACATA
AAGACACGGCTGGAGCAGGAGATCGCTACTTACCGCAGCCTGCTCGAGGGCC
AGGATGCCAAGATGGCTGGCATTGGCATCAGGGAAGCCTCTTCAGGAGGTGG
TGGTAGCAGCAGCAATTTCCACATCAATGTAGAAGAGTCAGTGGATGGACAG
GTGGTTTCTTCCCACAAGAGAGAAATCTAAGTGTCTATTGCAGGAGAAACGT
CCCTTGCCACTCCCCACTCTCATCAGGCCAAGTGGAGGACTGGCCAGAGGGC
CTGCACATGCAAACTCCAGTCCCTGCCTTCAGAGAGCTGAAAAGGGTCCCTC
GGTCTTTTATTTCAGGGCTTTGCATGCGCTCTATTCCCCCTCTGCCTCTCCCCA
CCTTCTTTGGAGCAAGGAGATGCAGCTGTATTGTGTAACAAGCTCATTTGTAC
AGTGTCTGTTCATGTAATAAAGAATTACTTTTCCTTTTGCAAAT-3'
UC Clone #57 (SEQ ID NO:3) semenogelin II,
GenBank Accession #M81652

5'AGACAAGATTTTTCAAGCAAGATGAAGTCCATCATCCTCTTTGTCCTTTCCC
TGCTCCTTATCTTGGAGAAGCAAGCAGCTGTGATGGGACAAAAAGGTGGATC
AAAAGGCCAATTGCCAAGCGGATCTTCCCAATTTCCACATGGACAAAAGGGC
CAGCACTATTTTGGACAAAAAGACCAACAACATACTAAATCCAAAGGCAGTT
TTTCTATTCAACACACATATCATGTAGACATCAATGATCATGACTGGACCCGA
AAAAGTCAGCAATATGATTTGAATGCCCTACATAAGGCGACAAAATCAAAAC
AACACCTAGGTGGAAGTCAACAACTGCTCAATTATAAACAAGAAGGCAGAG
ACCATGATAAATCAAAAGGTCATTTTCACATGATAGTTATACATCATAAAGG
AGGCCAAGCTCATCATGGGACACAAAATCCTTCTCAAGATCAGGGGAATAGC
CCATCTGGAAAGGGATTATCCAGTCAATGTTCAAACACAGAAAAAAGGCTAT
GGGTTCATGGACTAAGTAAAGAACAAGCTTCAGCCTCTGGTGCACAAAAAGG
TAGAACACAAGGTGGATCCCAAAGCAGTTATGTTCTCCAAACTGAAGAACTA
GTAGTTAACAAACAACAACGTGAGACTAAAAATTCTCATCAAAATAAAGGGC
ATTACCAAAATGTGGTTGACGTGAGAGAGGAACATTCAAGTAAACTACAAAC
TTCACTCCATCCTGCACATCAAGACAGACTCCAACATGGACCCAAAGACATT
TTTACTACCCAAGATGAGCTCCTAGTATATAACAAGAATCAACACCAGACAA
AAAATCTCAGTCAAGATCAAGAGCATGGCCGGAAGGCACATAAAATATCATA
CCCGTCTTCACGTACAGAAGAAAGACAACTTCACCATGGAGAAAAGAGTGTA
CAGAAAGATGTATCCAAAGGCAGCATTTCTATCCAAACTGAAGAGAAAATAC
ATGGCAAGTCTCAAAACCAGGTAACAATTCATAGTCAAGATCAAGAGCATGG
CCATAAGGAAAATAAAATATCATACCAATCTTCAAGTACAGAAGAAAGACAT
CTCAACTGTGGAGAAAAGGGCATCCAGAAAGGTGTATCCAAAGGCAGTATTT
CGATCCAAACTGAAGAGCAAATACATGGCAAGTCTCAAAACCAGGTAAGAA

TABLE 2-continued

DNA Sequences of Prostate Markers

TTCCTAGTCAAGCTCAAGAGTATGGCCATAAGGAAAATAAAATATCATACCA
ATCTTCGAGTACAGAAGAAAGACGTCTCAACAGTGGAGAAAAGGATGTACA
GAAAGGTGTATCCAAAGGCAGTATTTCTATCCAAACTGAAGAGAAAATACAT
GGCAAGTCTCAAAACCAGGTAACAATTCCTAGTCAAGATCAAGAGCATGGCC
ATAAGGAAAATAAAATGTCATACCAATCTTCAAGTACAGAAGAAAGACGACT
CAACTATGGAGGAAAGAGCACGCAGAAAGATGTATCCCAAAGCAGTATTTCT
TTCCAAATTGAAAAGCTAGTAGAAGGCAAGTCTCAAATCCAGACACCAAATC
CTAATCAAGATCAATGGTCTGGCCAAAATGCAAAAGGAAAGTCTGGTCAATC
TGCAGATAGCAAACAAGACCTACTCAGTCATGAACAAAAAGGCAGATACAA
ACAGGAATCCAGTGAGTCACATAATATTGTAATTACTGAGCATGAGGTTGCC
CAAGATGATCATTTGACACAACAATATAATGAAGACAGAAATCCAATATCTA
CATAGCCCTGTTGCTTAGCAACCACTTGAAAAGCTGGACCAATAGCAAGGTG
TCACCCGACCTCAGTGAAGTCTTTGATGTTTCTGAGAGGCAGACTCCCATGTG
GTCCCAGATCCTTGGTCCATGGATGACACCACCTTCCCATGCTTCCTTGCATT
AGGCTTTCTAAACCCGGAGCCCCTTCAAACTTCCAATAAAGGGATCATTTTCT
GCTTT-3'

Example 4

Relative Quantitative Reverse Transcriptase-PolymeraseChain Reaction-

The inventors have described the identification by Southern Differential Hybridization of candidate genes that were partial cDNA fragments. This necessitated the use of a relatively quantitative approach to independently confirm the differential expression of the mRNAs from which these partial cDNA fragments were derived. The key objective of the described screening protocol is the assessment of changes in the relative abundances of mRNA.

The reverse transcription-polymerase chain reaction (RT-PCR) protocols described in the following examples were developed as a means to determine the relative abundances of mRNA species that are expressed in various tissues, organs and cells. This protocol has been described as applied to prostate tissue in U.S. application Ser. No. 08/692,787, incorporated in relevant part herein by reference. Although the present example is drawn to the identification and confirmation of differential expression in various physiological states in prostate tissue and peripheral blood cells, the methods described herein may be applied to any type of tissue to provide a sensitive method of identifying differential expression.

In the practice of this method, total cell RNA is first converted into cDNA using reverse transcriptase primed with random hexamers. This protocol results in a cDNA population in which each RNA has contributed according to its relative proportion in original total cell RNA. If two RNA species differ by ten fold in their original relative abundances in the total cell RNA, then the cDNA derived from these two RNAs will also differ by ten fold in their relative abundances in the resulting population of cDNA. This is a conservation of relative proportionality in the conversion of RNA to cDNA.

Since both reverse transcription and PCR may be performed in such a way as to conserve proportionality, it is possible to compare the relative abundance of an mRNA species in two or more total cell RNA populations by first converting the RNA to cDNA and then amplifying a fragment of the cDNA derived from the specific mRNA by PCR. The ratio of the amplified masses of the targeted cDNAs is very close to or identical to the ratios of the mRNAs in the original total cell RNA populations.

Two preferred methods for RNA isolation are the guanidinium thiocyanate method, which is well known in the art, and kits for RNA isolation manufactured by Qiagen, Inc. (Chatworth, Calif.), with the kits being the most preferred for convenience.

The RNAs are digested with DNaseI to remove all genomic DNA that was co-isolated with the total cell RNA. Prior to DNaseI digestion, the RNA is in a particulate suspension in 70% ethanol. Approximately 50 µg of RNA (as determined by $OD_{260/280}$) is removed from the suspension and precipitated. This RNA is resuspended in DEPC treated sterile water. To this is added 10× DNaseI buffer (200 mM Tris-HCl; pH 8.4, 20 mM $MgCl_2$, 500 mM KCl), 10 units of RNase Inhibitor (GIBCO-BRL Cat#15518-012) and 20 units of DNaseI (GIBCO-BRL #18068-015). The volume is adjusted to 50 µl with additional DEPC treated water. The reaction is incubated at 37° C. for 30 minutes. After DNaseI digestion the RNAs are organic solvent-extracted with phenol and chloroform followed by ethanol precipitation. This represents the second ethanol precipitation of the isolated RNA. Empirical observations suggest that this repeated precipitation improves RNA performance in the RT reaction to follow.

Following DNaseI digestion, an aliquot of the RNA suspension in ethanol is removed and divided into thirds. A different procedure is performed on each one of the aliquot thirds. These three procedures are: (1). An $OD_{260/280}$ is obtained using a standard protocol and is used to estimate the amount of RNA present and its likely quality. (2). An aliquot is run out on an agarose gel, and the RNA is stained with ethidium bromide. Observation that both the 28S and 18S RNAs are visible as discreet bands and that there is little staining above the point at which the 28S rRNA migrates indicate that the RNA is relatively intact. While it is not critical to assay performance that the examined RNAs be completely free of partial degradation, it is important to determine that the RNA is not so degraded as to significantly effect the appearance of the 28S rRNA. (3). The total cell RNAs are run using a PCR-based test that confirms that the DNaseI treatment actually digested the contaminating genomic DNA to completion. It is very important to confirm complete digestion of genomic DNA because genomic DNA may act as a template in PCR reactions resulting in false positive signals in the relative quantitative RT-PCR assay described below. The assay for contaminating genomic DNA utilizes gene specific oligonucleotides that flank a 145 nucleotide long intron (intron #3) in the gene encoding Prostate Specific Antigen (PSA). This is a single copy gene with no pseudogenes. It is a member of the kallikrein gene family of serine proteases, but the oligonucleotides used in this assay are specific to PSA. The sequences of these oligonucleotides are:

5'CGCCTCAGGCTGGGGCAGCATT 3', SEQ ID NO:4 and
5'ACAGTGGAAGAGTCTCATTCGAGAT 3', SEQ ID NO:5.

In the assay for contaminating genomic DNA, 500 ng to 1.0 μg of each of the DNaseI treated RNAs are used as templates in a standard PCR (35–40 cycles under conditions described below) in which the oligonucleotides described above are used as primers. Human genomic DNA is used as the appropriate positive control. This DNA may be purchased from a commercial vendor. A positive signal in this assay is the amplification of a 242 nucleotide genomic DNA specific PCR product from the RNA sample being tested as visualized on an ethidium bromide stained electrophoretic gel. There should be no evidence of genomic DNA as indicated by this assay in the RNAs used in the RT-PCR assay described below. Evidence of contaminating genomic DNA results in re-digestion of the RNA with DNaseI and reevaluation of the DNase treated RNA by determining its $OD_{260/280}$ ratio, examination on electrophoretic gel and re-testing for genomic DNA contamination using the described PCR assay.

The standard conditions used for PCR (as mentioned in the last paragraph) are: 1× GIBCO-BRL PCR reaction buffer [20 mM Tris-Cl (pH 8.4), 50 mM Kcl], 1.5 mM $MgCl_2$, 200 μM each of the four dNTPs, 200 nM each oligonucleotide primer, concentration of template as appropriate, and 2.5 units of Taq polymerase per 100 μl of reaction volume. Using these conditions, PCR is performed with 35–40 cycles of: 94° C. for 45 sec, 55°–60° C. for 45 sec, and 72° C. for 1 minute.

Reverse transcription reactions are performed using the Superscript™ Preamplification System for First Strand cDNA Synthesis kit which is manufactured by GIBCO-BRL LifeTechnologies (Gaithersburg, Md.). Superscript™ is a cloned form of M-MLV reverse transcriptase that has been deleted for its endogenous RNase H activity in order to enhance its processivity. In the present example, the published protocols of the manufacturer are used for cDNA synthesis primed with random hexamers. cDNA synthesis may also be primed with a mixture of random hexamers (or other small oligonucleotides of random sequence) and oligo dT. The addition of oligo dT increases the efficiency of conversion of RNA to cDNA proximal to the polyA tail. As template, either 5 or 10 micrograms of RNA is used (depending on availability). After the RT reaction has been completed according to the protocol provided by GIBCO-BRL, the RT reaction is diluted with water to a final volume of 100 μl.

In the present examples, cDNAs made from total cell RNAs are normalized to contain equal concentrations of amplifiable β-actin cDNA. One μl of each diluted RT reaction is subjected to PCR using oligonucleotides specific to β-actin as primers. These primers are designed to cross introns, permitting the differentiation of cDNA and genomic DNA. These β-actin specific oligonucleotides have the sequences:

5'CGAGCTGCCTGACGGCCAGGTCATC 3', SEQ ID NO:6
and
5'GAAGCATTTGCGGTGGACGATGGAG 3', SEQ ID NO:7

PCR is performed under standard conditions as described previously for either 19 or 20 cycles. The resulting PCR product is 415 nucleotides in length. The product is examined by PCR using agarose gel electrophoresis followed by staining with ethidium bromide. The amplified cDNA fragment is then visualized by irradiation with ultra violet light using a transilluminator. A white light image of the illuminated gel is captured by an IS-1000 Digital Imaging System manufactured by Alpha Innotech Corporation. The captured image is analyzed using either version 2.0 or 2.01 of the software package supplied by the manufacturer to determine the relative amounts of amplified β-actin cDNA in each RT reaction.

To normalize the various cDNAs, water is added to the most concentrated cDNAs as determined by the assay described in the last paragraph. PCR using 1 μl of the newly rediluted and adjusted cDNA is repeated using the β-actin oligonucleotides as primers. The number of cycles of PCR must be increased to 21 or 22 cycles in order to compensate for the decreased concentrations of the newly diluted cDNAs. With this empirical method the cDNAs may be adjusted by dilution to contain roughly equal concentrations of amplifiable cDNA. Sometimes this process must be repeated to give acceptable final normalization. By dividing the average optical density of all observed bands by that of a particular band, a normalization statistic may be created that will permit more accurate comparisons of the relative abundances of RNAs examined in the normalized panel of cDNAs.

Once the normalization statistics are derived, PCR may be performed using different gene specific oligonucleotides as primers to determine the relative abundances of other mRNAs as represented as cDNAs in the normalized panel of diluted RT reaction products. The relative intensities of the bands is then adjusted and normalized to β-actin expression by multiplying the intensity quantities by the normalization statistics derived.

To determine quantitative differences in mRNA expression, it is necessary that the data is collected in the linear portion of the respective PCR amplification curves. This is technically difficult because currently used means of DNA quantitation are only sensitive enough to quantify the PCR products when they are approaching concentrations at which the product strands begin to compete with the primers for annealing. This means that the PCR products may only be detected at the very end of the linear range of the amplification curve. Predicting in advance at what cycle number the PCR products should be quantified is technically difficult.

To overcome these limitations, a two tiered approach was used to relatively quantify mRNA abundance levels using RT-PCR. In the first tier, pools of cDNAs produced by combining equal amounts of normalized cDNA are examined to determine how mRNA abundances vary in the average individual with a particular physiological state. This reduces the number of compared samples to a very small number such as two to four. In the studies described herein, two pools are examined. These are pools of normal individuals and those individuals with metastatic prostate disease. Each pool may contain a large number of individuals. While this approach does not discriminate differences between individuals, it may easily discern broad patterns of differential expression. The great advantage of examining pooled cDNAs is that it permits many duplicate PCR reactions to be simultaneously set up.

The individual duplicates may be harvested and examined at different cycle numbers of PCR. In a preferred method, four duplicate PCR reactions are set up. One duplicate is collected at 31, 34, 37, and 40 PCR cycles. Occasionally, PCR reactions are also collected at 28 cycles. Examining the PCRs at different cycle numbers yields the following benefits. It is very likely that at least one of the RT-PCRs will be in the optimum portion of the amplification curves to reliably compare relative mRNA abundances. In addition, the optimum cycle number will be known, so that studies with much larger sample sizes are much more likely to succeed. This is the second tier of a two tiered approach that has been taken to relatively quantify mRNA abundance levels using RT-PCR. Doing the RT-PCR with the pooled samples permits much more efficient application of RT-PCR than samples derived from individuals. A further benefit is that tube to tube variability in PCR may be discounted and controlled because most studies yield multiple data points due to duplication.

Like the previously described protocol involving individuals, the first step in this protocol is to normalize the pooled samples to contain equal amounts of amplifiable cDNA. This is done using oligonucleotides that direct the amplification of β-actin. In this example, a PCR amplification of a cDNA fragment derived from the β-actin mRNA from pools of normal individuals and individuals with metastatic prostate cancer was performed. This study was set up as four identical PCR reactions. The products of these PCRs were collected and electrophoresed after 22, 25, 28 and 31 PCR cycles. Quantitation of these bands using the IS 1000 system showed that the PCRs were still in the linear ranges of their amplification curves at 22, 25 and 28 cycles but that they left linearity at 31 cycles. This is known because the ratios of the band intensities remain constant and internally consistent for the data obtained from 22, 25 and 28 cycles, but these ratios become distorted at 31 cycles. This quantitation will also permit the derivation of normalizing statistics for the three pools relative to each other in exactly the same manner as was done previously for individuals.

This study is then repeated using gene specific primers for a gene other than β-actin. The intensities of the relevant bands were quantitated using the IS 1000 and normalized to the β-actin signals.

The central question to be answered in analyzing this data is whether the PCRs have been examined in the linear portions of their amplification curves. A test for this may be devised by determining if the proportionality of the PCR products has been conserved as PCR cycle number has increased. If the ratio between the two pools of a given PCR product remains constant with increasing cycle number, this is strong evidence that the PCRs were in the linear portions of their amplification curves when these observations were made. (This is better conservation of proportionality than is frequently observed. In some studies, data was excepted when the ratios were similar but not identical.) This conservation of proportionality was lost at 40 cycles. This indicates that these PCRs are nearing the plateau phases of their amplification curves.

The final major consideration to quantifying relative mRNA abundances with RT-PCR is tube to tube variability in PCR. This may result from many factors, including unequal heating and cooling in the thermocycler, imperfections in the PCR tubes and operator error. To control for this source of variation, the Cole-Parmer digital thermocouple Model #8402-00 was used to calibrate the thermocyclers used in these studies. Only slight variations in temperature were observed.

The RT-PCR protocol examining pooled cDNAs is internally controlled for tube to tube variability that might arise from any source. By examining the abundance of the PCR products at several different cycle numbers, it may be determined that the mass of the expected PCR product is increasing appropriately with increasing PCR cycle number. Not only does this demonstrate that the PCRs are being examined in the linear phase of the PCR, where the data is most reliable, it demonstrates that each reaction with the same template is consistent with the data from the surrounding cycle numbers. If there was an unexplained source of variation, the expectation that PCR product mass would increase appropriately with increasing cycle number would not be met. This would indicate artifactual variation in results. Internal duplication and consistency of the data derived from different cycle numbers controls for system derived variation in tube to tube results.

As described in the preceding paragraphs, the RT-PCR protocol using pooled cDNA templates overcomes the last two barriers to effective relative quantitative RT-PCR. These barriers are the need examine the PCR products while the reactions are in the linear portions of their amplification curves and the need to control tube to tube variation in PCR. The described protocol examines PCR products at three to four different cycle numbers. This insures that the PCRs are quantitated in their linear ranges and, as discussed in the last paragraph, controls for possible tube to tube variation.

In addition, the cycle number of PCR needed to detect β-actin cDNA from the diluted RT reactions, usually between 19 and 22 cycles, is sufficiently low to discount any contribution that genomic DNA might make to the abundance of amplifiable β-actin templates.

For the genes isolated in this study, total cell RNA was isolated from metastatic prostate cancer or buffy coat cells as described above. cDNA was made from one to five μg of each isolated RNA. All cDNAs were normalized for similar amounts of β-actin cDNA by RT-PCR. RT-PCR products were electrophoresed through agarose.

For relative quantitative RT-PCR with an external standard, quantitation of band intensities on ethidium bromide stained gels was performed using the IS-1000 image analysis system manufactured by the Alpha Innotech Corp. A normalizing statistic was generated for each cDNA sample, as the average of all β-actin signals divided by the β-actin signal for each cDNA sample respectively. Data for each sample was then normalized by multiplying the observed densitometry observation by the individual normalizing statistics. Normalized values predict differences in the steady state abundances of the respective mRNAs in the original total cell RNA samples.

This protocol resulted in the discovery that the expression of two cDNAs, UC Clone #51 (SEQ ID NO:1), UC Clone #56 (SEQ ID NO:2), was down regulated in metastatic prostate cancer, and the expression of one cDNA, UC Clone #57 (SEQ ID NO:3), was down regulated in the peripheral blood of metastatic prostate cancer patients.

UC Clone #51 (SEQ ID NO: 1) was confirmed by relative quantitative RT-PCR, at 32 cycles of amplification, to be down regulated in metastatic prostate cancer tissues in comparison to normal prostate and organ confined prostate cancer, including BPH. The data was normalized against β-actin mRNA. This gene was down-regulated to the point of its expression being totally inhibited in metastatic cancer patients when compared with normal and BPH individuals. Such a clear contrast in regulation makes this gene an excellent marker for the detection of malignant prostate tumors in biopsy samples containing a mixture of normal, benign and malignant prostate cells.

UC Clone #56 (SEQ ID NO:2) was confirmed by relative quantitative RT-PCR, at 32 cycles of amplification, to be down regulated in metastatic prostate cancer tissues in comparison to normal prostate and organ confined prostate cancer, including BPH. The data was normalized against β-actin mRNA. This gene was down-regulated in metastatic cancer patients compared with normal and BPH individuals, making it a useful marker for metastatic prostate cancer.

UC Clone #57 (SEQ ID NO:3) was not differentially regulated in prostate cancer tissues compared to normal prostate. However, relative quantitative RT-PCR of UC Clone #57 (semenogelin II) determined, at 40 cycles of amplification, the gene's expression was down regulated in the blood of individuals with metastatic prostate cancer compared to normal individuals. Those who are skilled in the art will recognize the usefulness of a metastatic prostate marker that can be easily obtained from peripheral blood, as opposed to collection from a prostate tissue biopsy.

Of the genes quantitated with these primers, prostate-specific transglutaminase (GenBank Accession #s L34840, I20492) and cytokeratin 15 (GenBank Accession #X07696) are more abundant in normal and BPH glands and are complemplated to be tumor suppressors. Semenogelin II (GenBank Accession #M81652 and M81651) is more abundant in the peripheral blood of patients with metastatic prostate cancer and is contemplated to be a progression marker.

The oligonucleotides used for relative quantitative RT-PCR are listed in Table 3. These sequences are designated herein as SEQ ID NO:8, matches GenBank Accession #s L34840, I20492, prostate-specific transglutaminase Nt 548–571; SEQ ID NO:9, matches GenBank Accession #s L34840, I20492, prostate-specific transglutaminase: Nt 742–765 (antisense strand); SEQ ID NO:10, matches GenBank Accession #X07696, cytokeratin 15 Nt 1337–1359; SEQ ID NO:11, matches GenBank Accession #X07696, cytokeratin 15 Nt 1586–1608 (antisense strand); SEQ ID NO:12, matches GenBank Accession #M81652 semenogelin II Nt 1089–1116; SEQ ID NO:13, matches GenBank Accession #M81652, semenogelin II Nt 1697–1724 (antisense strand).

TABLE 4

Genes Whose mRNAs have Abundances that Vary in Prostate Disease Relative to Normal Individuals

| Name of cDNA Fragment | Sequence Determined | Confirmed by Northern analysis | Confirmed by RT-PCR | Previously Known |
|---|---|---|---|---|
| UC Clone #51 (SEQ ID NO: 1) | Yes | Yes | Yes | GB #L34840, GB #I20492 |
| UC Clone #56 (SEQ ID NO: 2) | Yes | No | Yes | GB #X07696 |
| UC Clone #57 (SEQ ID NO: 3) | Yes | Yes | Yes | GB #M81652 |

It will be recognized that the genes and gene products (RNAs and proteins) for the above described markers of prostate disease are included within the scope of the disclosure herein described. It will also be recognized that the diagnosis and prognosis of prostatic disease by detection of the nucleic acid products of these genes are included within the scope of the present invention. Serological and other assays to detect these mRNA species or their translation products are also indicated. It is obvious that these assays are of utility in diagnosing metastatic cancers derived from prostate and other tissues.

Those practiced in the art will realize that there exists naturally occurring genetic variation between individuals. As a result, some individuals may synthesize prostate-specific transglutaminase, cytokeratin 15, or semenogelin II gene products that differ from those described by the sequences entailed in the Genbank number listed above. We include in our definition of "synthesize prostate-specific transglutaminase, cytokeratin 15, or semenogelin II," those products encoded by prostate-specific transglutaminase, cytokeratin 15, or semenogelin II genes that vary in sequence from those described above. Those practiced in the art will realize that modest variations in DNA sequence will not significantly obscure the identity of a gene product as being derived from the synthesize prostate-specific transglutaminase, cytokeratin 15, or semenogelin genes.

TABLE 3

Oligonucleotides used in the relative quantitative RT-PCR portion of these studies.

Oligonucleotides used to examine the expression of genes:
Prostate-specific transglutaminase (SEQ ID NO:1), GenBank Accession #L34840, I20492.

5'GGGGGCTGCCAGAAGTATCAAATG3', SEQ ID NO:8
    5'TGCCACCTTCGTAGTCCCCAGTCC3', SEQ ID NO:9
Cytokeratin 15 (SEQ ID NO:2), GenBank Accession #X07696.

5'TCTTCAGGAGGTGGTGGTAGCAG3', SEQ ID NO:10
    5'GAGAGGCAGAGGGGGAATAGAGC3', SEQ ID NO:11
Semenogelin II (SEQ ID NO:3), GenBank Accession #M81652 and M81651.

5'ACATCTCAACTGTGGAGAAAAGGGCATC3', SEQ ID NO:12
    5'TGATCATCTTGGGCAACCTCATGCTCAG3', SEQ ID NO:13
Controls used to normalize relative quantitative RT-PCR
Prostate Specific Antigen (PSA)

5'CGCCTCAGGCTGGGGCAGCATT3', SEQ ID NO:4
    5'ACAGTGGAAGAGTCTCATTCGAGAT3', SEQ ID NO:5.
β-actin 5'CGAGCTGCCTGACGGCCAGGTCATC3', SEQ ID NO:6
    5'GAAGCATTTGCGGTGGACGATGGAG3', SEQ ID NO:7

A summary of experiments performed to confirm the aforementioned genes as prostate disease markers are shown below in Table 4.

All of the compositions and methods disclosed and claimed herein may be made and executed without undue experimentation in light of the present disclosure. While the compositions and methods of this disclosure have been described in terms of preferred embodiments, it is apparent that variations may be applied to the composition, methods and in the steps or in the sequence of steps of the method described herein without departing from the concept, spirit and scope of the invention.

More specifically, it is apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. patent application Ser. No. 08/692,787
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,215,051
U.S. Pat. No. 4,275,149
U.S. Pat. No. 4,277,437
U.S. Pat. No. 4,366,241
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,797,368
U.S. Pat. No. 4,800,159
U.S. Pat. No. 4,883,750
U.S. Pat. No. 4,946,773
U.S. Pat. No. 4,959,317
U.S. Pat. No. 5,139,941
U.S. Pat. No. 5,168,053
U.S. Pat. No. 5,262,311
U.S. Pat. No. 5,279,721,
U.S. Pat. No. 5,354,855
U.S. Pat. No. 5,624,824
U.S. Pat. No. 5,624,830
U.S. Pat. No. 5,625,047
WO 88/10315.
WO 89/06700.
EPO 0273085
EPO 329822

Abremski and Hoess, 1992.
Abremski et al., "Properties of a mutant Cre protein that alters the topological linkage of recombinant products," *J. Mol. Biol.*, 202:59–66, 1988.
Abuin and Bradley, "Recycling selectable markers in mouse embryonic stem cells," *Mol. Cell. Biol.*, 16:1851–1856, 1996.
Alcaraz et al., *Cancer Res.*, 55:3998–4002, 1994.
Alt et al., *J. Biol. Chem.*, 253:1357, 1978.
Andrews et al., "The FLP recombinase of the 2 micron circle DNA of yeast: interaction wit its target sequences," *Cell*, 40:795–803, 1985.
Antibodies: A Laboratory Manual, Cold Spring Harbor Laboratory, Cold Spring Harbor Press, Cold Spring Harbor, N.Y., 1988.
Austin et al., "A novel role for site-specific recombination in maintenance of bacterial replicons," *Cell*, 25:729–736, 1981.
Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.
Bellus, *J. Macromol. Sci. Pure Appl. Chem*, A31(1): 1355–1376, 1994.
Berzal-Herranz et al., *Genes and Devel.*, 6:129–134, 1992.
Bittner et al., *Methods in Enzymol*, 153:516–544, 1987.
Bookstein et al., *Proc. Nat'l Acad. Sci. USA*, 87:7762–7767, 1990b.
Bookstein et al., *Science*, 247:712–715, 1990a.
Boring et al., *CA-Cancer J. Pract.*, 43:7–26, 1993.
Bova et al., *Cancer Res.*, 53:3869–3873, 1993.
Campbell, In: *Monoclonal Antibody Technology, Laboratory Techniques in Biochemistry and Molecular Biology*, Burden and Von Knippenberg, Eds., Vol. 13:75–83, Elsevier, Amsterdam, 1984.
Capaldi et al., *Biochem. Biophys. Res. Comm.*, 76:425, 1977.
Carter and Coffey, In: *Prostate Cancer: The Second Tokyo Symposium*, J. P. Karr and H. Yamanak (eds.), pp. 19–27, New York: Elsevier, 1989.
Carter and Coffey, *Prostate*, 16:39–48, 1990.
Carter et al., *Proc. Nat'l Acad. Sci. USA* 93:749–753, 1996.
Carter et al., *Proc. Nat'l Acad. Sci. USA*, 87:8751–8755, 1990.
Cech et al., "In vitro splicing of the ribosomal RNA precursor of Tetrahymena: involvement of a guanosine nucleotide in the excision of the intervening sequence," *Cell*, 27:487–496, 1981.
Chalfie et al., *Science*, 263:802–805, 1994.
Chang et al., "Foreign gene delivery and expression in hepatocytes using a hepatitis B virus vector," Hepatology, 14:134A, 1991.
Chen and Okayama, "High-efficiency transformation of mammalian cell by plasmid DNA," *Mol. Cell. Biol.* 7:2745–2752, 1987.
Chowrira et al., "In vitro and in vivo comparison of hammerhead, hairpin, and hepatitis delta virus self-processing ribozyme cassetyes," *J. Biol. Chem.*, 269:25856–25864, 1994.
Chowrira et al., *Biochemistry*, 32:1088–1095, 1993.
Clark et al., "Cell lines for the production of recombinant adeno-associated virus," *Human Gene Therapy*, 6:1329–1341, 1995.
Coffin, "Retroviridae and their replication," In: Virology, Fields et al. (eds.), New York: Raven Press, pp. 1437–1500, 1990.
Colbere-Garapin et al., *J. Mol. Biol.*, 150:1, 1981.
Cookson et al., *J. Urol.*, 157(2):673–676, 1997.
Cotten et al., "High efficiency receptor-mediated delivery of small and large (48 kilobase) gene constructs using the endosome disruption activity of defective or inactivated adenovirus particles," *Proc. Natl. Acad. Sci. USA*, 89:6094–6098, 1992.
Couch et al., "Immunization with types 4 and 7 adenovirus by selective infection of the intestinal tract," *Am. Rev. Resp. Dis.*, 88:394–403, 1963.
Coupar et al., "A general method for the construction of recombinant vaccinia virus expressing multiple foreign genes," Gene, 68:1–10, 1988.
Cumo and Oettinger, "Analysis of regions of RAG-2 important for V(D)J recombination," *Nuc. Acids Res.*, 22(10): 1810–1814, 1994.

Curiel, "Gene transfer mediated by adenovirus-polylysine DNA complexes," In: *Viruses in Human Gene Therapy*, J.-M. H. Vos (Ed.), Carolina Academic Press, Durham, N.C., pp. 179–212, 1994.

Dale and Ow, "Gene transfer with subsequent removal of the selection gene from the host genome," *Proc. Natl. Acad. Sci. USA*, 88:10558–10562, 1991.

Damaj et al., *FASEB J.* 10:1426–1434, 1996.

Dbom, *J. Cancer Res. Clin. Oncol.*, 106:210–218, 1983.

Diamond et al., *J. Urol.*, 128:729–734, 1982.

Dong et al., *Science*, 268:884–886, 1995.

Dong et al., *Cancer Res.*, 56(19):4387–4390, 1996.

Fechheimer et al., "Transfection of mammalian cells with plasmid DNA by scrape loading and sonication loading," *Proc. Natl. Acad. Sci. USA* 84:8463–8467, 1987.

Flotte et al., "An improved system for packaging recombinant adeno-associated virus vectors capable of in vivo transduction," *Gene Therapy*, 2:29–37, 1995.

Flotte et al., "Gene expression from adeno associated virus vector in airway epithelial cells," *Am. J. Respir. Cell Mol. Biol.*, 7:349–356, 1992.

Forster and Symons, "Self-cleavage of plus and minus RNAs of a virusoid and a structural model for the active sites," *Cell*, 49:211–220, 1987.

Fraley and Kaplan, "Entrapment of a bacterial plasmid in phospholipid vesicles:potential for gene transfer," *Proc. Nat'l. Acad. Sci. USA* 76:3348–3352, 1979.

Freifelder, *Physical Biochemistry Applications to Biochemistry and Molecular Biology*, 2nd ed., Wm. Freeman and Co., New York, N.Y., 1982.

Friedmann, "Progress toward human gene therapy," *Science*, 244:1275–1281, 1989.

Frohman, *PCR™ Protocols: A Guide to Methods and Applications*, Academic Press, N.Y., 1990.

Gefter et al., *Somatic Cell Genet.*, 3:231–236, 1977.

Gerlach et al., "Construction of a plant disease resistance gene from the satellite RNA of tobacco rinspot virus," *Nature (London)*, 328:802–805, 1987.

Ghosh-Choudhury et al., "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Goding, In: *Monoclonal Antibodies: Principles and Practice*, 2d ed., Orlando, Fla., Academic Press, pp. 60–61, 65–66, 71–74, 1986.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Gopal, "Gene transfer method for transient gene expression, stable transformation, and cotransformation of suspension cell cultures," *Mol. Cell. Biol.* 5:1188–1190, 1985.

Graham and Prevec, "Adenovirus-based expression vectors and recombinant vaccines," *Biotechnology*, 20:363–390, 1992.

Graham and Prevec, "Manipulation of adenovirus vectors," In: *Gene Transfer and Expression Protocols*, Murray, E. J., ed., Humana, New Jersey, vol. 7, 109–128, 1991.

Graham and Van Der Eb, "A new technique for the assay of infectivity of human adenovirus 5 DNA," *Virology* 52:456–467, 1973.

Graham et al., "Characteristics of a human cell line transformed by DNA from human adenovirus type 5", *J. Gen. Virol.*, 36:59–72, 1977.

Grunhaus and Horwitz, "Adenovirus as cloning vector," *Seminar in Virology*, 3:237–252, 1992.

Harland and Weintraub, "Translation of mRNA injected into *Xenopus* oocytes is specifically inhibited by antisense RNA," *J. Cell Biol.* 101:1094–1099, 1985.

Haseloff and Gerlach, "Simple RNA enzymes with new and highly specific endoribonuclease activities," *Nature*, 334:585–591, 1988.

Hermonat and Muzyczka, "Use of adeno-associated virus as a mammalian DNA cloning vector; transduction of neomycin resistance into mammalian tissue culture cells," *Proc. Nat'l. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l. Acad. Sci. USA* 90:2812–2816, 1993.

Hess et al., *J. Adv. Enzyme Reg.*, 7:149, 1968.

Hitzeman et al., *J. Biol. Chem.*, 255:2073, 1980.

Hoess et al., "P1 site-specific recombination: nucleotide sequence of the recombining sites," *Proc. Natl. Acad Sci. USA*, 79:3398–3402, 1982.

Holland et al., *Biochemistry*, 17:4900, 1978.

Holmes et al., *Prostate*, 27:25–29, 1996.

Horoszewicz, Kawinski and Murphy, *Anticancer Res.*, 7:927–936, 1987.

Horwich et al. "Synthesis of hepadenovirus particles that contain replication-defective duck hepatitis B virus genomes in cultured HuH7 cells," *J. Virol.*, 64:642–650, 1990.

Huang et al., *Prostate*, 23: 201–212, 1993.

Innis et al., *PCR Protocols*, Academic Press, Inc., San Diego Calif., 1990.

Inouye et al., *Nucleic Acids Res.*, 13:3101–3109, 1985.

Isaacs et al., *Cancer Res.*, 51:4716–4720, 1991.

Isaacs et al., Seminars in Oncology, 21:1–18, 1994.

Israeli et al., *Cancer Research*, 54:1807–1811, 1994.

Johnson et al., In: *Biotechnology and Pharmacy*, Pezzuto et al., Eds., Chapman and Hall, New York, 1993.

Jones and Shenk, "Isolation of deletion and substitution mutants of adenovirus type 5," *Cell*, 13:181–188, 1978.

Jones, *Genetics*, 85:12, 1977.

Joyce, "RNA evolution and the origins of life," *Nature*, 338:217–244, 1989.

Kaneda et al., "Increased expression of DNA cointroduced with nuclear protein in adult rat liver," *Science*, 243:375–378, 1989.

Kaplitt et al., "Long-term gene expression and phenotypic correction suing adeno-associated virus vectors in the mammalian brain," *Nature Genetics*, 8:148–154, 1994.

Karlsson et al., *EMBO J.*, 5:2377–2385, 1986.

Kasahara et al., *Science*, 266:1373–1376, 1994.

Kato et al., "Expression of hepatitis β virus surface antigen in adult rat liver," *J. Biol. Chem.*, 266:3361–3364, 1991.

Kaufman, "Selection and Coamplification of Heterologous Genes in Mammalian Cells," *Methods in Enzymology*, 185:537–566, 1990.

Kelleher and Vos, "Long-term episomal gene delivery in human lymphoid cells using human and avian adenoviral-assisted transfection," *Biotechniques*, 17(6):1110–1117, 1994.

Kim and Cech, "Three dimensional model of the active site of the self-splicing rRNA precursor of Tetrahymena," *Proc. Natl. Acad. Sci. USA*, 84:8788–8792, 1987.

Kingsman et al., *Gene*, 7:141, 1979.

Klein et al., "High-velocity microprojectiles for delivering nucleic acids into living cells," Nature, 327:70–73, 1987.

Kohler and Milstein, Eur. J. Immunol., 6: 511–519, 1976.

Kohler and Milstein, Nature, 256:495–497, 1975.

Koller and Smithies, 1992.

Kotin et al., "Site-specific integration by adeno-associated virus," Proc. Natl. Acad. Sci. USA, 87:2211–2215, 1990.

Kwoh et al., Proc. Nat. Acad. Sci. USA, 86:1173, 1989.

LaFace et al., "Gene transfer into hematopoietic progenitor cells mediated by an adeno-associated virus vector," Viology, 162:483–486, 1988.

Lakso et al., "Efficient in vivo manipulation of mouse genomic sequences at the zygote stage," Proc. Nat. Acad. Sci. USA, 93:5860–5865, 1996.

Laughlin et al., "Latent Infection of KB Cells with Adeno-Associated Virus Type 2," J. Virol., 60:515–524, 1986.

Le Gal La Salle et al., "An adenovirus vector for gene transfer into neurons and glia in the brain," Science, 259:988–990, 1993.

Lebkowski et al., "Adeno-associated virus: a vector system for efficient introduction and integration of DNA into a variety of mammalian cell types," Mol. Cell. Biol., 8:3988–3996, 1988.

Lee et al., Canc. Epidemiol. Biomarkers Prev., 6(6): 443–450, 1997.

Levrero et al., "Defective and nondefective adenovirus vectors for expressing foreign genes in vitro and in vivo," Gene, 101:195–202, 1991.

Lilja, H., Proc. Natl. Acad. Sci. USA. 89(10): 4559–4563 1992.

Lowy et al., Cell, 22:817, 1980.

Luo et al., "Adeno-associated virus 2 mediated transfer and functional expression of a gene encoding the human granulocyte-macrophage colony-stimulating factor," Blood,82 (Supp.): 1,303A, 1994.

Macoska et al., Cancer Res., 54:3824–3830, 1994.

Maeser and Kahmann, "The Gin recombinase of phage Mu can catalyze site-specific recombination in plant protoplasts," Mol. Gen. Genetics, 230:170–176, 1991.

Mann et al., "Construction of a retrovirus packaging mutant and its use to produce helper-free defective retrovirus," Cell, 33:153–159, 1983.

Markowitz et al., "A safe packaging line for gene transfer: Separating viral genes on two different plasmids," J. Virol., 62:1120–1124, 1988.

McCarty et al., "Sequences Required for Coordinate Induction of Adeno-Associated Virus p19 and p40 Promoters by Rep Protein," J. Virol., 65:2936–2945, 1991.

McLaughlin et al., "Adeno-Associated Virus General Transduction Vectors: Analysis of Proviral Structures," J. Virol., 62:1963–1973, 1988.

Michel and Westhof, "Modeling of the three-dimensional architecture of group I catalytic introns based on comparative sequence analysis," J. Mol. Biol., 216:585–610, 1990.

Miller, Curr. Top. Microbiol. Immunol., 158:1, 1992.

Morton et al., Cancer Res., 53:3585–3590, 1993a.

Morton et al., In: CANCER MEDICINE (3rd Ed.), Holland, J. F., Frei III, E., Bast Jr., C. C. (eds), Lea and Febiger, Philadelphia, Pa., pp. 1793–1824, 1993b.

Mulligan et al., Proc. Nat'l Acad. Sci. USA, 78:2072, 1981.

Murphy et al., Cancer, 78: 809–818, 1996.

Murphy et al., Prostate, 26:164–168, 1995.

Murray et al., J. Pathol., 177(2):147–152, 1995.

Muzyczka, "Use of Adeno-Associated Virus as a General Transduction Vector for Mammalian Cells," Curr. Top. Microbiol Immunol., 158:97–129, 1992.

Nakamura et al., In: Handbook of Experimental Immunology (4th Ed.), Weir, E., Herzenberg, L. A., Blackwell, C., Herzenberg, L. (eds), Vol. 1, Chapter 27, Blackwell Scientific Publ., Oxford, 1987a.

Nakamura et al., In: Enzyme Immunoassays: Heterogeneous and Homogeneous Systems, Chapter 27, 1987b.

Nicolas and Rubinstein, "Retroviral vectors," In: Vectors: A survey of molecular cloning vectors and their uses, Rodriguez and Denhardt (eds.), Stoneham: Butterworth, pp. 494–513, 1988.

Nicolau and Sene, "Liposome-mediated DNA transfer in eukaryotic cells: dependence of the transfer efficiency upon the type of liposomes used and the host cell cycle stage," Biochim. Biophys. Acta, 721:185–190, 1982

Nicolau et al., "Liposomes as carriers for in vivo gene transfer and expression," Methods Enzymol., 149:157–176, 1987.

O'Dowd et al., J. Urol., 158(3 Pt. 1):687–698, 1997.

O'Hare et al., Proc. Nat'l Acad Sci. USA, 78:1527, 1981.

Oettinger et al., "RAG-1 and RAG-2, adjacent genes that synergistically activate V(D)J recombination," Science, 248:1517–1523, 1990.

Ohara et al., Proc. Nat'l Acad. Sci. USA, 86:5673–5677, 1989.

Onouchi et al., "Visualization of site-specific recombination catalyzed by a recombinase from Zygo-saccharomyces rouxii in Arabidopsis thaliana," Mol. Cell. Biol., 247:653–660, 1995.

Palukaitis et al., "Characterization of a viroid associated with avocado sunblotch disease," Virology, 99:145–151, 1979.

Partin and Oesterling, J. Urol., 152:1358–1368, 1994.

Partin et al., Cancer Res., 53:744–746, 1993.

Paskind et al., "Dependence of moloney murine leukemia virus production on cell growth," Virology, 67:242–248, 1975.

Pearsons et al., J. Urol., 150:120–125, 1993.

Perales et al., Proc. Natl. Acad. Sci. USA, 91:4086–4090, 1994.

Perriman et al., "Extended target-site specificity for a hammerhead ribozyme," Gene, 113:157–163, 1992.

Piironen et al., Clin. Chem. 42: 1034–1041, 1996.

Potter et al., "Enhancer-dependent expression of human k immunoglobulin genes introduced into mouse pre-B lymphocytes by electroporation," Proc. Natl Acad. Sci. USA, 81:7161–7165, 1984.

Prody et al., "Autolytic processing of dimeric plant virus satellite RNA." Science, 231:1577–1580, 1986.

Qiao et al., Biochem. Biophys. Res. Comm., 201:581–588, 1994.

Racher et al., Biotechnology Techniques, 9:169–174, 1995.

Ragot et al., "Efficient adenovirus-mediated transfer of a human minidystrophin gene to skeletal muscle of mdx mice," Nature, 361:647–650, 1993.

Reinhold-Hurek and Shub, "Self-splicing introns in tRNA genes of widely divergent bacteria," Nature, 357:173–176, 1992.

Renan, "Cancer genes: current status, future prospects, and applicants in radiotherapy/oncology," Radiother. Oncol., 19:197–218, 1990.

Rich et al., "Development and analysis of recombinant adenoviruses for gene therapy of cystic fibrosis," Hum. Gene Ther., 4:461–476, 1993.

Ridgeway, "Mammalian expression vectors," In: Vectors: A survey of molecular cloning vectors and their uses. Rodriguez and Denhardt, eds. Stoneham: Butterworth, pp. 467–492, 1988.

Rippe et al., "DNA-mediated gene transfer into adult rat hepatocytes in primary culture," *Mol. Cell Biol.,* 10:689–695, 1990.

Rosenfeld et al., "Adenovirus-mediated transfer of a recombinant α1-antitrypsin gene to the lung epithelium in vivo," *Science,* 252:431–434,1991.

Rosenfeld et al., "In vivo transfer of the human cystic fibrosis transmembrane conductance regulator gene to the airway epithelium," *Cell,* 68:143–155,1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079–9083, 1989.

Sager et al., *FASEB J.,* 7:964–970, 1993.

Saito et al., *Biochem. Biophys. Res. Commun.,* 200:378, 1994.

Sambrook et al., (ed.), *MOLECULAR CLONING,* Cold Spring Harbor Laboratory Press, Cold Spring Harbor, N.Y., 1989.

Sambrook, Fritsch, Maniatis, *Molecular Cloning: A Laboratory Manual,* 2nd Ed., Cold Spring Harbor Press, Cold Spring Harbor, N.Y., 1989.

Samulski et al., "Helper-free stocks of recombinant adeno-associated viruses: Normal integration does not require viral gene expression," *J. Virol.,* 63:3822–3828, 1989.

Samulski et al., "Targeted integration of adeno-associated virus (AAV) into human chromosome 19," *EMBO J.,* 10:3941–3950, 1991.

Santerre et al., *Gene,* 30:147, 1984.

Sarver et al., "Ribozymes as potential anti-HIV-1 therapeutic agents," *Science,* 247:1222–1225, 1990.

Sauer, "Functional expression of the cre-lox site-specific recombination system in the yeast *Saccharoyces cerevisiae*," *Mol. Cell. Biol.,* 7:2087–2096, 1987.

Sauer, "Manipulation of transgenes by site-specific recombination: Use of Cre recombinase," *Methods in Enzymology,* 225:890–900, 1993.

Scanlon et al., "Ribozyme-mediated cleavages of c-fos mRNA reduce gene expression of DNA synthesis enzymes and metallothionein," *Proc Natl Acad Sci USA,* 88:10591–10595, 1991.

Schatz et al., "The V(D)J recombination activating gene, RAG-1, *Cell,* 59:1035–1048, 1989.

Shelling and Smith, "Targeted integration of transfected and infected adeno-associated virus vectors containing the neomycin resistance gene," *Gene Therapy,* 1:165–169, 1994.

Sidransky et al., *Science,* 252:706–709, 1991.

Silver et al, *Clin. Cancer Res.,* 3:81–85, 1997.

Sioud et al., "Preformed ribozyme destroys tumour necrosis factor mRNA in human cells," *J. Mol. Biol.,* 223:831–835, 1992.

Smith, U.S. Pat. No. 4,215,051

Sternberg and Hamilton, "Bacteriophage P1 site-specific recombination. 1. Recombination between lox P sites," *J. Mol. Biol.,* 150:467–486, 1981.

Sternberg et al., "Bacteriophage P1 cre gene and its regulatory region," *J. Mol. Bio.,* 187:197–212, 1986.

Stinchcomb et al., *Nature,* 282:39, 1979.

Stratford-Perricaudet and Perricaudet, In: *Human Gene Transfer,* Eds, Cohen-Haguenauer and Boiron, Editions John Libbey Eurotext, France, pp. 51–61, 1991.

Stratford-Perricaudet et al, *Hum. Gene. Ther.,* 1:241–256, 1991.

Symons, "Avocado sunblotch viroid: primary sequence and proposed secondary structure." *Nucl. Acids Res.,* 9:6527–6537, 1981.

Symons, "Small catalytic RNAs." *Annu. Rev. Biochem.,* 61:641–671, 1992.

Szybalska et al., *Proc. Nat'l Acad. Sci. USA,* 48:2026, 1962.

Takahashi et al., *Cancer Res.,* 54:3574–3579, 1994.

Taparowsky et al., *Nature,* 300:762–764, 1982.

Temin, "Retrovirus vectors for gene transfer: Efficient integration into and expression of exogenous DNA in vertebrate cell genome," In: *Gene Transfer,* Kucherlapati (ed.), New York: Plenum Press, pp. 149–188, 1986.

Thompson et al., "Decreased expression of BRCA1 accelerates growth and is often present during sporadic breast cancer progression," *Nature Genet.,* 9:444–450, 1995.

Top et al., "Immunization with live types 7 and 4 adenovirus vaccines. II. Antibody response and protective effect against acute respiratory disease due to adenovirus type 7,"*J. Infect. Dis.,* 124:155–160, 1971.

Tratschin et al., "A human parvovirus, adeno-associated virus, as a eucaryotic vector: transient expression and encapsidation of the procaryotic gene for chloramphenicol acetyltransferase," *Mol. Cell. Biol.,* 4:2072–2081, 1984.

Tratschin et al., "Adeno-associated virus vector for high-frequency integration, expression and rescue of genes in mammalian cells," *Mol. Cell. Biol.,* 5:32581–3260, 1985.

Tschemper et al., *Gene,* 10:157, 1980.

Tur-Kaspa et al., "Use of electroporation to introduce biologically active foreign genes into primary rat hepatocytes," *Mol. Cell Biol.,* 6:716–718, 1986.

Umbas et al., *Cancer Res.,* 52:5104–5109, 1992.

Veltri, *J. Cell. Biochem. Suppl.,* 19:249–258, 1994.

Visakorpi et al., *Am. J. Pathol.,* 145:1–7, 1994.

Wagner et al., *Science,* 260:1510–1513, 1990.

Walker et al., Proc. Nat'l Acad. Sci. USA, 89:392–396, 1992.

Walsh et al., "Phenotypic correction of Fanconi anemia in human hematopoietic cells with a recombinant adeno-associated virus vector," *J. Clin. Invest.,* 94:1440–1448, 1994.

Wei et al., "Expression of the human glucocerebrosidase and arylsulfatase A genes in murine and patient primary fibroblasts transduced by an adeno-associated virus vector," *Gene Therapy,* 1:261–268, 1994.

Wigler et al., *Cell,* 11:223, 1977.

Wigler et al., *Proc. Nat'l Acad. Sci. USA,* 77:3567, 1980.

Wigley et al., "Site-specific transgene insertion: an approach," *Reprod. Fertil. Dev.,* 6:585–588, 1994.

Wingo et al., *CA Cancer J. Clin.,* 47(4):239–242, 1997.

Wong et al., "Appearance of β-lactamase activity in animal cells upon liposome mediated gene transfer," *Gene,* 10:87–94, 1980.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Wu et al., *Genomics,* 4:560, 1989.

Yang et al., "Characterization of cell lines that inducibly express the adeno-associated virus Rep proteins," *J. Virol.,* 68:4847–4856, 1994.

Yang et al., "In vivo and in vitro gene transfer to mammalian somatic cells by particle bombardment," *Proc. Nat'l Acad. Sci. USA,* 87:9568–9572, 1990.

Yoder et al., "In vivo gene transfer in murine hematopoietic reconstituting stem cells mediated by the adeno-associated virus 2-based vectors," *Blood,* 82 (Supp.): 1:347A, 1994.

Yuan and Altman, "Selection of guide sequences that direct efficient cleavage of mRNA by human ribonuclease P," *Science,* 263:1269–1273, 1994.

Yuan et al., "Targeted cleavage of mRNA by human RNase P," *Proc. Natl. Acad. Sci. USA,* 89:8006–8010, 1992.

Zhou et al., "Adeno-associated virus 2 mediated gene transfer in murine hematopoietic cells, *Exp. Hematol.* (NY), 21:928–933, 1993.

Zhou, et al., "Adeno-associated virus 2-mediated high efficiency gene transfer into immature and mature subsets of hematopoietic progenitor cells in human umbilical cord blood," *J. Exp. Med.,* 179:1867–1875, 1994.

---

What is claimed is:

1. A method of diagnosing metastatic prostate cancer in a subject, comprising the steps of:
   (a) obtaining one or more test samples from prostate tissue or serum or both of said subject; and
   (b) detecting a decrease in quantity of expression of a metastatic prostate cancer marker gene selected from prostate-specific transglutaminase, cytokeratin 15, or semenogelin II or a combination thereof in said test samples;
   wherein a decrease in quantity of expression of prostate-specific transglutaminase or cytokeratin 15 in a test sample from prostate tissue or of semenogelin II in a test sample from serum is diagnostic for metastatic prostate cancer.

2. The method of claim 1, further defined as comprising the step of:
   (a) comparing the quantity of expression of one or more of said markers to the quantity of expression of the same marker or markers expressed in a control sample obtained from prostate tissue or serum or both of one or more individuals known not to have metastatic prostate cancer;
   (b) wherein a decrease in quantity of expression in said test sample compared to the control sample is indicative of metastatic prostate cancer.

3. The method of claim 1 in which said marker gene is a prostate-specific transglutaminase gene.

4. The method of claim 1 in which said marker gene is a cytokeratin 15 gene.

5. The method of claim 1 in which said marker gene is a semenogelin II gene.

6. The method of claim 3, wherein said prostate-specific transglutaminase gene encodes the sequence designated as SEQ ID NO:1 or its complement.

7. The method of claim 4, wherein said cytokeratin 15 gene encodes the sequence designated as SEQ ID NO:2 or its complement.

8. The method of claim 5, wherein said semenogelin II gene encodes the sequence designated as SEQ ID NO:3 or its complement.

9. The method of claim 1, further defined as comprising the step of obtaining or detecting ribonucleic acids from said samples.

10. The method of claim 9, wherein said detecting is further defined as contacting said ribonucleic acids with a probe that hybridizes under high stringency conditions with an RNA product of said marker genes to obtain a hybridized product.

11. The method of claim 10, wherein said detecting is by Northern hybridization or in situ hybridization.

12. The method of claim 10, further comprising determining the amount of hybridized product.

13. The method of claim 10 in which the sequence of said probe is selected to bind specifically to a prostate-specific transglutaminase, cytokeratin 15, or semenogelin II mRNA or product thereof.

14. The method of claim 10 in which the sequence of said probe is selected to bind specifically to a prostate-specific transglutaminase mRNA or product thereof.

15. The method of claim 10 in which the sequence of said probe is selected to bind specifically to a cytokeratin 15 mRNA or product thereof.

16. The method of claim 10 in which the sequence of said probe is selected to bind specifically to a semenogelin II mRNA or product thereof.

17. The method of claim 13 wherein said oligonucleotide probe is selected to bind specifically to an isolated nucleic acid having a sequence or its complement selected from a group consisting of SEQ ID NO:1, SEQ ID NO:2 and SEQ ID NO:3.

18. The method of claim 9, wherein said ribonucleic acids are amplified to form nucleic acid amplification products.

19. The method of claim 18, wherein said amplification is by RT-PCR.

20. The method of claim 19, wherein said amplification comprises contacting said ribonucleic acids with a pair of amplification primers designed to amplify a prostate-specific transglutaminase, cytokeratin 15, or semenogelin II mRNA.

21. The method of claim 20, wherein said amplification comprises contacting said ribonucleic acids with a pair of amplification primers designed to amplify a nucleic acid segment comprising a detectable segment of a nucleic acid having the sequence or complement of SEQ ID NO:1, SEQ ID NO:2 or SEQ ID NO:3.

22. The method of claim 21, wherein said detectable segment is from about 100 bases in length up to about the length of the coding sequences of SEQ ID NO:1, SEQ ID NO:2 or SEQ ID NO:3.

23. The method of claim 1, further defined as detecting difference in quantity of expression of a prostate-specific transglutaminase, cytokeratin 15 or semenogelin II polypeptide.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 3064 base pairs
        (B) TYPE: nucleic acid
        (C) STRANDEDNESS: single
        (D) TOPOLOGY: linear (xi) SEQUENCE DESCRIPTION: SEQ ID NO:1:

```
AATTCTAAAA ATGCTTTTGC AAGCTTGCAT GCCTGCAGGT GCAGCGGCCG CCAGTGTGAT      60

GGATATCTGC AGAATTCGGC TTGCGCTCAG CTGGAATTCC GCAGAGATAG AGTCTTCCCT     120

GGCATTGCAG GAGAGAATCT GAAGGGATGA TGGATGCATC AAAAGAGCTG CAAGTTCTCC     180

ACATTGACTT CTTGAATCAG GACAACGCCG TTTCTCACCA CACATGGGAG TTCCAAACGA     240

GCAGTCCTGT GTTCCGGCGA GGACAGGTGT TTCACCTGCG GCTGGTGCTG AACCAGCCCC     300

TACAATCCTA CCACCAACTG AAACTGGAAT TCAGCACAGG GCCGAATCCT AGCATCGCCA     360

AACACACCCT GGTGGTGCTC GACCCGAGGA CGCCCTCAGA CCACTACAAC TGGCAGGCAA     420

CCCTTCAAAA TGAGTCTGGC AAAGAGGTCA CAGTGGCTGT CACCAGTTCC CCCAATGCCA     480

TCCTGGGCAA GTACCAACTA AACGTGAAAA CTGGAAACCA CATCCTTAAG TCTGAAGAAA     540

ACATCCTATA CCTTCTCTTC AACCCATGGT GTAAAGAGGA CATGGTTTTC ATGCCTGATG     600

AGGACGAGCG CAAAGAGTAC ATCCTCAATG ACACGGGCTG CCATTACGTG GGGGCTGCCA     660

GAAGTATCAA ATGCAAACCC TGGAACTTTG GTCAGTTTGA GAAAAATGTC CTGGACTGCT     720

GCATTTCCCT GCTGACTGAG AGCTCCCTCA AGCCCACAGA TAGGAGGGAC CCCGTGCTGG     780

TGTGCAGGGC CATGTGTGCT ATGATGAGCT TTGAGAAAGG CCAGGGCGTG CTCATTGGGA     840

ATTGGACTGG GGACTACGAA GGTGGCACAG CCCCATACAA GTGGACAGGC AGTGCCCCGA     900

TCCTGCAGCA GTACTACAAC ACGAAGCAGG CTGTGTGCTT TGGCCAGTGC TGGGTGTTTG     960

CTGGGATCCT GACTACAGTG CTGAGAGCGT TGGGCATCCC AGCACGCAGT GTGACAGGCT    1020

TCGATTCAGC TCACGACACA GAAAGGAACC TCACGGTGGA CACCTATGTG AATGAGAATG    1080

GCGAGAAAAT CACCAGTATG ACCCACGACT CTGTCTGGAA TTTCCATGTG TGGACGGATG    1140

CCTGGATGAA GCGACCCTAC GACGGCTGGC AGGCTGTGGA CGCAACGCCG CAGGAGCGAA    1200

GCCAGGGTGT CTTCTGCTGT GGGCCATCAC CACTGACCGC CATCCGCAAA GGTGACATCT    1260

TTATTGTCTA TGACACCAGA TTCGTCTTCT CAGAAGTGAA TGGTGACAGG CTCATCTGGT    1320

TGGTGAAGAT GGTGAATGGG CAGGAGGAGT TACACGTAAT TTCAATGGAG ACCACAAGCA    1380

TCGGGAAAAA CATCAGCACC AAGGCAGTGG GCCAAGACAG GCGGAGAGAT ATCACCTATG    1440

AGTACAAGTA TCCAGAAGGC TCCTCTGAGG AGAGGCAGGT CATGGATCAT GCCTTCCTCC    1500

TTCTCAGTTC TGAGAGGGAG CACAGACAGC CTGTAAAAGA GAACTTTCTT CACATGTCGG    1560
```

```
TACAATCAGA TGATGTGCTG CTGGGAAACT CTGTTAATTT CACCGTGATT CTTAAAAGGA    1620

AGACCGCTGC CCTACAGAAT GTCAACATCT TGGGCTCCTT TGAACTACAG TTGTACACTG    1680

GCAAGAAGAT GGCAAAACTG TGTGACCTCA ATAAGACCTC GCAGATCCAA GGTCAAGTAT    1740

CAGAAGTGAC TCTGACCTTG GACTCCAAGA CCTACATCAA CAGCCTGGCT ATATTAGATG    1800

ATGAGCCAGT TATCAGAGGT TTCATCATTG CGGAAATTGT GGAGTCTAAG GAAATCATGG    1860

CCTCTGAAGT ATTCACGTCA AACCAGTACC CTGAGTTCTC TATAGAGTTG CCTAACACAG    1920

GCAGAATTGG CCAGCTACTT GTCTGCAATT GTATCTTCAA GAATACCCTG CCATCCCTT     1980

TGACTGACGT CAAGTTCTCT TTGGAAAGCC TGGGCATCTC CTCACTACAG ACCTCTGACC    2040

ATGGGACGGT GCAGCCTGGT GAGACCATCC AATCCCAAAT AAAATGCACC CCAATAAAAA    2100

CTGGACCCAA GAAATTTATC GTCAAGTTAA GTTCCAAACA AGTGAAAGAG ATTAATGCTC    2160

AGAAGATTGT TCTCATCACC AAGTAGCCTT GTCTGATGCT GTGGAGCCTT AGTTGAGATT    2220

TCAGCATTTC CTACCTTGTG CTTAGCTTTC AGATTATGGA TGATTAAATT TGATGACTTA    2280

TATGAGGGCA GATTCAAGAG CCAGCAGGTC AAAAAGGCCA ACACAACCAT AAGCAGCCAG    2340

ACCCACAAGG CCAGGTCCTG TGCTATCACA GGGTCACCTC TTTTACAGTT AGAAACACCA    2400

GCCGAGGCCA CAGAATCCCA TCCCTTTCCT GAGTCATGGC CTCAAAAATC AGGGCCACCA    2460

TTGTCTCAAT TCAAATCCAT AGATTTCGAA GCCACAGAGC TCTTCCCTGG AGCAGCAGAC    2520

TATGGGCAGC CCAGTGCTGC CACCTGCTGA CGACCCTTGA GAAGCTGCCA TATCTTCAGG    2580

CCATGGGTTC ACCAGCCCTG AAGGCACCTG TCAACTGGAG TGCTCTCTCA GCACTGGGAT    2640

GGGCCTGATA GAAGTGCATT CTCCTCCTAT TGCCTCCATT CTCCTCTCTC TATCCCTGAA    2700

ATCCAGGAAG TCCCTCTCCT GGTGCTCCAA GCAGTTTGAA GCCCAATCTG CAAGGACATT    2760

TCTCAAGGGC CATGTGGTTT TGCAGACAAC CCTGTCCTCA GGCCTGAACT CACCATAGAG    2820

ACCCATGTCA GCAAACGGTG ACCAGCAAAT CCTCTTCCCT TATTCTAAAG CTGCCCCTTG    2880

GGAGACTCCA GGGAGAAGGC ATTGCTTCCT CCCTGGTGTG AACTCTTTCT TTGGTATTCC    2940

ATCCACTATC CTGGCAACTC AAGGCTGCTT CTGTTAACTG AAGCCTGCTC CTTCTTGTTC    3000

TGCCCTCCAG AGATTTGCTC AAATGATCAA TAAGCTTTAA ATTAAACCGG AATCCGCGGA    3060

ATTC                                                                3064

(2) INFORMATION FOR SEQ ID NO:2:

(i) SEQUENCE CHARACTERISTICS:
        (A) LENGTH: 1709 base pairs
        (B) TYPE: nucleic acid
        (C) STRANDEDNESS: single
        (D) TOPOLOGY: linear (xi) SEQUENCE DESCRIPTION: SEQ ID NO:2:

GGTACCTCCT GCCAGCACCT CTTGGGTTTG CTGAGAACTC ACGGGCTCCA GCTACCTGGC      60

CATGACCACC ACATTTCTGC AAACTTCTTC CTCCACCTTT GGGGGTGGCT CAACCCGAGG     120

GGGTTCCCTC CTGGCTGGGG GAGGTGGCTT TGGTGGGGGG AGTCTCTCTG GGGGAGGTGG     180

AAGCCGAAGT ATCTCAGCTT CTTCTGCTAG GTTTGTCTCT TCAGGGTCAG GAGGAGGATA     240

TGGGGGTGGC ATGAGGGTCT GTGGCTTTGG TGGAGGGGCT GGTAGTGTTT TCGGTGGAGG     300

CTTTGGAGGG GGCGTTGGTG GGGTTTTGG TGGTGGCTTT GGTGGTGGCG ATGGTGGTCT      360

CCTCTCTGGC AATGAGAAAA TTACCATGCA GAACCTCAAT GACCGCCTGG CCTCCTACCT     420

GGACAAGGTA CGTGCCCTGG AGGAGGCCAA TGCTGACCTG GAGGTGAAGA TCCATGACTG     480

GTACCAGAAG CAGACCCCAG CCAGCCCAGA ATGCGACTAC AGCCAATACT TCAAGACCAT     540
```

```
TGAAGAGCTC CGGGACAAGA TCATGGCCAC CACCATCGAC AACTCCCGGG TCATCCTGGA      600

GATCGACAAT GCCAGGCTGG CTGCGGACGA CTTCAGGCTC AAGTATGAGA ATGAGCTGGC      660

CCTGCGCCAG GGCGTTGAGG CTGACATCAA CGGCTTGCGC CGAGTCCTGG ATGAGCTGAC      720

CCTGGCCAGG ACTGACCTGG AGATGCAGAT CGAGGGCCTG AATGAGGAGC TAGCCTACCT      780

GAAGAAGAAC CACGAAGAGG AGATGAAGGA GTTCAGCAGC CAGCTGGCCG GCCAGGTCAA      840

TGTGGAGATG GACGCAGCAC CGGGTGTGGA CCTGACCCGT GTGCTGGCAG AGATGAGGGA      900

GCAGTACGAG GCCATGGCGG AGAAGAACCG CCGGGATGTC GAGGCCTGGT TCTTCAGCAA      960

GACTGAGGAG CTGAACAAAG AGGTGGCCTC CAACACAGAA ATGATCCAGA CCAGCAAGAC     1020

GGAGATCACA GACCTGAGAC GCACGATGCA GGAGCTGGAG ATCGAGCTGC AGTCCCAGCT     1080

CAGCATGAAA GCTGGGCTGG AGAACTCACT GGCCGAGACA GAGTGCCGCT ATGCCACGCA     1140

GCTGCAGCAG ATCCAGGGGC TCATTGGTGG CCTGGAGGCC CAGCTGAGTG AGCTCCGATG     1200

CGAGATGGAG GCTCAGAACC AGGAGTACAA GATGCTGCTT GACATAAAGA CACGGCTGGA     1260

GCAGGAGATC GCTACTTACC GCAGCCTGCT CGAGGGCCAG GATGCCAAGA TGGCTGGCAT     1320

TGGCATCAGG GAAGCCTCTT CAGGAGGTGG TGGTAGCAGC AGCAATTTCC ACATCAATGT     1380

AGAAGAGTCA GTGGATGGAC AGGTGGTTTC TTCCCACAAG AGAGAAATCT AAGTGTCTAT     1440

TGCAGGAGAA ACGTCCCTTG CCACTCCCCA CTCTCATCAG GCCAAGTGGA GGACTGGCCA     1500

GAGGGCCTGC ACATGCAAAC TCCAGTCCCT GCCTTCAGAG AGCTGAAAAG GGTCCCTCGG     1560

TCTTTTATTT CAGGGCTTTG CATGCGCTCT ATTCCCCCTC TGCCTCTCCC CACCTTCTTT     1620

GGAGCAAGGA GATGCAGCTG TATTGTGTAA CAAGCTCATT TGTACAGTGT CTGTTCATGT     1680

AATAAAGAAT TACTTTTCCT TTTGCAAAT                                       1709

(2) INFORMATION FOR SEQ ID NO:3:

(i) SEQUENCE CHARACTERISTICS:
        (A) LENGTH: 1981 base pairs
        (B) TYPE: nucleic acid
        (C) STRANDEDNESS: single
        (D) TOPOLOGY: linear (xi) SEQUENCE DESCRIPTION: SEQ ID NO:3:

AGACAAGATT TTTCAAGCAA GATGAAGTCC ATCATCCTCT TTGTCCTTTC CCTGCTCCTT       60

ATCTTGGAGA AGCAAGCAGC TGTGATGGGA CAAAAAGGTG GATCAAAAGG CCAATTGCCA      120

AGCGGATCTT CCCAATTTCC ACATGGACAA AAGGGCCAGC ACTATTTTGG ACAAAAAGAC      180

CAACAACATA CTAAATCCAA AGGCAGTTTT TCTATTCAAC ACACATATCA TGTAGACATC      240

AATGATCATG ACTGGACCCG AAAAAGTCAG CAATATGATT TGAATGCCCT ACATAAGGCG      300

ACAAAATCAA AACAACACCT AGGTGGAAGT CAACAACTGC TCAATTATAA CAAGAAGGC       360

AGAGACCATG ATAAATCAAA AGGTCATTTT CACATGATAG TTATACATCA TAAAGGAGGC      420

CAAGCTCATC ATGGGACACA AAATCCTTCT CAAGATCAGG GGAATAGCCC ATCTGGAAAG      480

GGATTATCCA GTCAATGTTC AAACACAGAA AAAAGGCTAT GGGTTCATGG ACTAAGTAAA      540

GAACAAGCTT CAGCCTCTGG TGCACAAAAA GGTAGAACAC AAGGTGGATC CCAAAGCAGT      600

TATGTTCTCC AAACTGAAGA ACTAGTAGTT AACAAACAAC AACGTGAGAC TAAAAATTCT      660

CATCAAAATA AAGGGCATTA CCAAAATGTG GTTGACGTGA GAGAGGAACA TTCAAGTAAA      720

CTACAAACTT CACTCCATCC TGCACATCAA GACAGACTCC AACATGGACC CAAAGACATT      780

TTTACTACCC AAGATGAGCT CCTAGTATAT AACAAGAATC AACACCAGAC AAAAAATCTC      840
```

-continued

```
AGTCAAGATC AAGAGCATGG CCGGAAGGCA CATAAAATAT CATACCCGTC TTCACGTACA        900

GAAGAAAGAC AACTTCACCA TGGAGAAAAG AGTGTACAGA AAGATGTATC CAAAGGCAGC        960

ATTTCTATCC AAACTGAAGA GAAAATACAT GGCAAGTCTC AAAACCAGGT AACAATTCAT       1020

AGTCAAGATC AAGAGCATGG CCATAAGGAA AATAAAATAT CATACCAATC TTCAAGTACA       1080

GAAGAAAGAC ATCTCAACTG TGGAGAAAAG GGCATCCAGA AAGGTGTATC CAAAGGCAGT       1140

ATTTCGATCC AAACTGAAGA GCAAATACAT GGCAAGTCTC AAAACCAGGT AAGAATTCCT       1200

AGTCAAGCTC AAGAGTATGG CCATAAGGAA AATAAAATAT CATACCAATC TTCGAGTACA       1260

GAAGAAAGAC GTCTCAACAG TGGAGAAAAG GATGTACAGA AAGGTGTATC CAAAGGCAGT       1320

ATTTCTATCC AAACTGAAGA GAAAATACAT GGCAAGTCTC AAAACCAGGT AACAATTCCT       1380

AGTCAAGATC AAGAGCATGG CCATAAGGAA AATAAAATGT CATACCAATC TTCAAGTACA       1440

GAAGAAAGAC GACTCAACTA TGGAGGAAAG AGCACGCAGA AAGATGTATC CCAAAGCAGT       1500

ATTTCTTTCC AAATTGAAAA GCTAGTAGAA GGCAAGTCTC AAATCCAGAC ACCAAATCCT       1560

AATCAAGATC AATGGTCTGG CCAAAATGCA AAAGGAAAGT CTGGTCAATC TGCAGATAGC       1620

AAACAAGACC TACTCAGTCA TGAACAAAAA GGCAGATACA AACAGGAATC CAGTGAGTCA       1680

CATAATATTG TAATTACTGA GCATGAGGTT GCCCAAGATG ATCATTTGAC ACAACAATAT       1740

AATGAAGACA GAAATCCAAT ATCTACATAG CCCTGTTGCT TAGCAACCAC TTGAAAAGCT       1800

GGACCAATAG CAAGGTGTCA CCCGACCTCA GTGAAGTCTT TGATGTTTCT GAGAGGCAGA       1860

CTCCCATGTG GTCCCAGATC CTTGGTCCAT GGATGACACC ACCTTCCCAT GCTTCCTTGC       1920

ATTAGGCTTT CTAAACCCGG AGCCCCTTCA AACTTCCAAT AAAGGGATCA TTTTCTGCTT       1980

T                                                                     1981
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

```
CGCCTCAGGC TGGGGCAGCA TT                                                22
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

```
ACAGTGGAAG AGTCTCATTC GAGAT                                             25
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

```
CGAGCTGCCT GACGGCCAGG TCATC                                             25
```

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

GAAGCATTTG CGGTGGACGA TGGAG                                           25

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

GGGGGCTGCC AGAAGTATCA AATG                                            24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

TGCCACCTTC GTAGTCCCCA GTCC                                            24

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

TCTTCAGGAG GTGGTGGTAG CAG                                             23

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

GAGAGGCAGA GGGGGAATAG AGC                                             23

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

ACATCTCAAC TGTGGAGAAA AGGGCATC                                     28

(2) INFORMATION FOR SEQ ID NO:13:

```
        (i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:13:

TGATCATCTT GGGCAACCTC ATGCTCAG                                           28

(2) INFORMATION FOR SEQ ID NO:14:

(i) SEQUENCE CHARACTERISTICS:
            (A) LENGTH: 8224 base pairs
            (B) TYPE: nucleic acid
            (C) STRANDEDNESS: single
            (D) TOPOLOGY: linear (xi) SEQUENCE DESCRIPTION: SEQ ID NO:14:

GAGCTCAGGC AATCCACCCG TCTTGGCCTC CCAAAGTGCT AGGATTACAG CCACCGTGCC         60

CAGCCCGAAT CAATGCAATT CTTATCAAAA ATTTTATGGC TTTCTTGTAG AAATGGAAAA        120

GTGGGTTCTA ACGTTCATTT GGAATTTCAA GGGATCCCAA ATAGCCGTAC AATCTTGACT        180

AAGAGGAACA CAGTTGGAAG ACTCACACTT CACAAATACT ATCTTATAAC CCATTATTTA        240

AACTGACAAC AACTTAACAC TGCTTCCATA AACAAACAAG AGAAAGAAAA CTAATAAAGA        300

CTCTATACTT TAACTTCATT CCCGCCACTT TTTAACTGAT AATTGCTGTG CTTTCTCTCA        360

CCCCATGCAC AGAAATGCTC TGTGCCCCAT ACCTGCAACC GGGAGATGAA GGAGGAGTGG        420

CATCAGTGAT ACAAGTGTTT TTCCTACCCC TTCAGCGCCT CTTTCAGTGA TATAAAGTTA        480

AAATCAGTTA CTGTGAGTGC TCACCTGATT TTTTGGTTCT TATAAAGGTG ATCTTTCTCT        540

GCAGATACTT GTTAAATTGG TGACCTTGGT GGGGCAGGG GGGATCATTG GAGCCTTCTA        600

TTCCACCATC TTGTTCTGCC ACCCTCCTCT CTTAATTTTT ATTCTCTCTG AACGATTTTA        660

TTTCTCCTTC ATTTCTGAAG GATAGCTTTG CTGAGGGTAA TGTTCTTAGC TGACAGTTTT        720

CTCTTTTAGT AATTTGAATA TATTATGCCA TTCTTTCCTG GCCTGTAAGG TTTCTCCCGA        780

GAAATTCTCT GTTAGTCAGA TGGGGGTTAC CTTATATGTG ACTTGACATT TTTCTCTTGC        840

TGCTTTTAAA AATCTTTCTT TGTCTTTGAC TTTTAGCAAT GCAATTAAAA TGTGCCTTGG        900

AGAGAACCCG TTTAGGTTGA ATTTATTTAG GGTTCTTATA GCTTCCTGGA CCTGGATTTC        960

TATCTCTCTC CCAAGATGCA AGAAGTTTTC TGCTATTATT TTATGCGTCT GATGGAAAAG       1020

TTGCCTCTTC CAATTTTATG GAGTAGATTT TATAAGCGAA AACTTATTTT TATGAATGGG       1080

TCTTTAGGTG TTAGTTCATT TGAGTTTGTT GGTTTTTGTT GCAGGTGTAT GTAGCAGTAT       1140

TGTTTCCATA GAGTTTCTTC ACCTATGATC CACACTTGTG GCACTTGAGA GTTTCTCAGC       1200

GCCCTAGTTG AGAGAGTGTG CTGCTACAGT GGCATGGCTT TGCCAGTGCT GTGGTTCCAG       1260

CGCTAATTCT CAGGTCAGGG GTGTGTGCAT CCACGTGGTA GGTAATTCAA TTAAGGTATG       1320

ACTCAATGGT ATTGGGGCCA GGGTGCTGTT ATCCTGGCTG GAAGCATGGG CACATGTTTG       1380

TTCAGTCAGT GAGTGTGACT ACAGGCTAGG GGTGGCCTGT GAAGCTGTTT CTTGGTTTCA       1440

GGACGTGGAA GTACAGCTTC TCAACTGGTC TGAAGACATG TCTGCCAGGG TCAGTCTACT       1500

GGGCTTTTTC TCAGGCCCAA GATGTGGGTG TAAGGCTGCT TGGATGGCCT ACGAGAGGAA       1560

GGGAATGAGA GAGGAAAGAG GGCTTTTTCT CAGGCACTTG ACACAGCTGC ATGGCTGAGT       1620

GGCTAGGCTT TGAGCATTTC TGTAAGGGGT GGCCCAAGAA GATATTCTGT AGGCCTAGGG       1680

TGTAGGCATG GAGCTTCTTG GTTGTCCTTC ATGTGTGACC ACCAGAGGCA ATCTGTAGGA       1740

CTGTTTCTCA GACCTGGGAC ATGACCACAT AACTACTTGG CTGGCTTGGG TATGCCCACC       1800
```

```
AGGGGTGGCC CATGGGCTGT TTCTCAGGTT TGGGAAATGG GCTCTCGGCA GCTGGGCCAG    1860

CGTGGTGTCA AGCCCAGCAG GGGAGCTTGT GAGTCTGTTT CTCAAGCTCT TATTGGGAGT    1920

ATAGGGCCAC TGAGCAGGCC ATGGATGTGT CTCTGGAGGG AGAGAGTGTT ACAGGGCTAT    1980

TTCTCAGGTA CTCAGTGTGG ACACATAGCC ACTGTGCTGC CACAGGGGCA TATAAACTGT    2040

GTCAAGCTCA GTGACCTGTC TCCTACTTGG TGAACTTTAA AATATTCTAC TATTTTTTCC    2100

TTGTTTATTT TTTATCATTT GATATTTTCC CAATCATGAT ACCACATCTA AGATGTATGC    2160

AGCACTATAC CATGTTTATG CTTTCCAAAT TACCGATTTC TGCTTTCATC TTTATCAATA    2220

GATTTATTTT TAATTTTGAA ATGCTTTTTT TTCAAATTTC ATTAAATCCA ATCATGATAT    2280

GAGTATCATA ATCACATGTT GTGCCTAGTT TGCATTTTCC TGCTTTGTTT TTGCAAATCT    2340

TGTGCACCTT TGTTTTATCT GTATCTTTTG GACACTAGAT TAGTTGGAAG TTTTGTTCTT    2400

GATCCATAAG TAAGATTAAT ATTTCAGACT CTTGTTTGTT CCGGTAATCT TGGAACACAA    2460

CAGTTCCTGG TATTTCCTTA AGGGAAGTGT AAGGAAGATT ATAGTGATTA GCAGGTACAG    2520

CAATAAATTT GTGTTCAGGA AAACTTTACT CTTTTCTTTT GGGGTCCCTG CCATAAGGAA    2580

ATACTTACTG CCCTTAGGGC AAACAGATAA AACTGGTAAG ATCTCAGAAT GGCTCATAGA    2640

GAAACCACAT AGCTCACATG CTTCAAGTTT GATGGCATAA GTAGCATTTT TTCCTATGGT    2700

TGGCCTTTCC CCTCTCCCCT TCCATATAGC ATTGCTTACA GGAAGGTTAG GATTTTAAGA    2760

GAGAATAATA GAAAATAAGT TTCCAAGCCG TCCTTTCTCC AGAACTACCC TCCACAGTGT    2820

TCTGAATGCA TACAGGGTCA CTGTTCAAAT GTTGCTGCTT CTCCTGTTGT CTTCTCATAA    2880

CAAGGACTTT TTCAGTCAAA GTAAAGAAAC TGGCCGGGTG CAGTGGCTCA TGCCTGTAAT    2940

CCCAGCAGTT TGGGAGGCTG AGGCGGGCGG ATCACGAGGT CAGGAGATTG AGACCATCCT    3000

GGCTAACACG GTGAAACCCC GTCTCTACTA AAAATACAAA AAATTAGCCG GGCGTGGTGG    3060

CAGGCACCTG TAGTCCCAGC TACTTGGGAA GCTGAGGCAG GAGAATGGCA TGAACCTGGG    3120

AGGCACAGCT TGCAGTGAGC CGAGATGGTG CCACTGCACT CCAGCCTGGG CGACAGAGCG    3180

AGACTCTGTC TCAAAAACAA ACAAACAAAA AAAACAAAAC AAACAAACAA ACAAACAAAA    3240

AACCTTCCTT GGATTTTTCA AGAAGTTTTC ACAATTGCAA AAAAACAAAA CAAAACAACA    3300

CAACACAACA AAACAAAACA AAAGCAAAAA AACCCTATGC TTCCACCCAA GGTAAAAATT    3360

TTAGCTTTAG GTCCACTCTC AATACATTAT TTAATGAACT GAAGTTGGCA ATATATTCCTC   3420

ACAGCCTGTT GGAGGGTTCA GCAGTTTATT ACAGAAGTAT GAAATGCTTT TATTTAAAAA    3480

ATGTATTTTG GTAAATACAT TTTTGTTTAG GTAAATATCA TCAAATAATC CAATTTGGAA    3540

ACCAACATTC TTACTTCTTT TTCCAACAGT TGTTCCTATC ATCATAAAAA CATGTTAAAT    3600

TTTTCTCATC CTTTCAAAAA ATCTCTGGAG CTTACCTCAC CCTCCAGATA CAGCCTCACC    3660

TCTCATTCCA CCATGAAATC AGACTTCTTG AGATGGTTTC AGCTGGACTC CATCCTTCAA    3720

CTGACAACCC AACACAACTG TATTCATCTC TCGTTAACAT TACTAGCAGT GAGTAACATC    3780

AGAAAGTTTT TGACACATGT TAGTCTTTTT TGTGATGAAC TTCACAGATA CATTTGACAT    3840

TGGTATGCCT CATTTATTTG TTGAAATTTT TTTCTTTGGC TTCCATGAAG TTTCTTTCTC    3900

TTCTGTATCA TTCTACTTCT ATGACTGCTC CTTCTCGAGT AAAACAGAAT GTGTCTCAGG    3960

ATTACTTTAA AACAAGACAA AGTATAGAGT TATACCTAAA ATTTAGTATT TAAGTTATTG    4020

GATCAGAAAG GAAACTCGCA TTTAGAGTAT GAAGGCATTG TCAGCCACCA ATTACTTTTG    4080

TAACCTGAAG CTAGTCTCCT TCCTACTCCG GACTGAATTT CTTCTGTATA ATGCAAGCGA    4140

TCTGGCATGA TGATATACAA AGACCGATAA AATTTTGCTG GGGATTCTGA AAGTAAAAAA    4200
```

```
AATTGCCTTT GATATTATGT CCCCATGCTA AGTCCCTGGG GACTTTGACA TTATCCCCCA    4260

CTGAGCAGGG GTGAGGAAGC TGGCATTTAC TAATAAGCTA TGAAAGGGCA GTGCCTTTTG    4320

ACATTTCAGC TCCACCCATA GCACACCCAC TCAAGGAACA TATAAATGAA GAGATCCGCT    4380

CAGTTCTCAG ACAAGATTTT TCAAGCAAGA TGAAGTCCAT CATCCTCTTT GTCCTTTCCC    4440

TGCTCCTTAT CTTGGAGAAG CAAGCAGCTG TGATGGGACA AAAAGGTGAG TGGAGAGGGT    4500

AAGCCTTGGG GAAAGCTACT TTAAAAAAAT GGCCTCTAAG GATATTCAGG GTGCAAACAG    4560

TAACCTGTTC AGGCACAGAT TCTTCTCCTT GATGAGAATT GATTTTTCTC CACCCAACGC    4620

TGTAGGCTTT TGGAAATATC AGAAATTTGT TGGGAAAAGG TGGGAGGTAA GAGTTGCAAG    4680

AGAGCTTTGG AGATAATGAA TGCATACATT TCTATTATCA ATTACCAGGT GGATCAAAAG    4740

GCCAATTGCC AAGCGGATCT TCCCAATTTC CACATGGACA AAAGGGCCAG CACTATTTTG    4800

GACAAAAAGA CCAACAACAT ACTAAATCCA AAGGCAGTTT TTCTATTCAA CACACATATC    4860

ATGTAGACAT CAATGATCAT GACTGGACCC GAAAAAGTCA GCAATATGAT TTGAATGCCC    4920

TACATAAGGC GACAAAATCA AAACAACACC TAGGTGGAAG TCAACAACTG CTCAATTATA    4980

AACAAGAAGG CAGAGACCAT GATAAATCAA AAGGTCATTT TCACATGATA GTTATACATC    5040

ATAAAGGAGG CCAAGCTCAT CATGGGACAC AAAATCCTTC TCAAGATCAG GGAATAGCC    5100

CATCTGGAAA GGGATTATCC AGTCAATGTT CAAACACAGA AAAAAGGCTA TGGGTTCATG    5160

GACTAAGTAA AGAACAAGCT TCAGCCTCTG GTGCACAAAA AGGTAGAACA CAAGGTGGAT    5220

CCCAAAGCAG TTATGTTCTC CAAACTGAAG AACTAGTAGT TAACAAACAA CAACGTGAGA    5280

CTAAAAATTC TCATCAAAAT AAAGGGCATT ACCAAAATGT GGTTGACGTG AGAGAGGAAC    5340

ATTCAAGTAA ACTACAAACT TCACTCCATC CTGCACATCA AGACAGACTC CAACATGGAC    5400

CCAAAGACAT TTTTACTACC CAAGATGAGC TCCTAGTATA TAACAAGAAT CAACACCAGA    5460

CAAAAAATCT CAGTCAAGAT CAAGAGCATG GCCGGAAGGC ACATAAAATA TCATACCCGT    5520

CTTCACGTAC AGAAGAAAGA CAACTTCACC ATGGAGAAAA GAGTGTACAG AAAGATGTAT    5580

CCAAAGGCAG CATTTCTATC CAAACTGAAG AGAAAATACA TGGCAAGTCT CAAAACCAGG    5640

TAACAATTCA TAGTCAAGAT CAAGAGCATG GCCATAAGGA AAATAAAATA TCATACCAAT    5700

CTTCAAGTAC AGAAGAAAGA CATCTCAACT GTGGAGAAAA GGGCATCCAG AAAGGTGTAT    5760

CCAAAGGCAG TATTTCGATC CAAACTGAAG AGCAAATACA TGGCAAGTCT CAAAACCAGG    5820

TAAGAATTCC TAGTCAAGCT CAAGAGTATG GCCATAAGGA AAATAAAATA TCATACCAAT    5880

CTTCGAGTAC AGAAGAAAGA CGTCTCAACA GTGGAGAAAA GGATGTACAG AAAGGTGTAT    5940

CCAAAGGCAG TATTTCTATC CAAACTGAAG AGAAAATACA TGGCAAGTCT CAAAACCAGG    6000

TAACAATTCC TAGTCAAGAT CAAGAGCATG GCCATAAGGA AAATAAAATG TCATACCAAT    6060

CTTCAAGTAC AGAAGAAAGA CGACTCAACT ATGGAGGAAA GAGCACGCAG AAAGATGTAT    6120

CCCAAAGCAG TATTTCTTTC CAAATTGAAA AGCTAGTAGA AGGCAAGTCT CAAATCCAGA    6180

CACCAAATCC TAATCAAGAT CAATGGTCTG GCCAAAATGC AAAAGGAAAG TCTGGTCAAT    6240

CTGCAGATAG CAAACAAGAC CTACTCAGTC ATGAACAAAA AGGCAGATAC AAACAGGAAT    6300

CCAGTGAGTC ACATAATATT GTAATTACTG AGCATGAGGT TGCCCAAGAT GATCATTTGA    6360

CACAACAATA TAATGAAGAC AGAAATCCAA TATCTACATA GCCCTGTTGC TTAGCAACCA    6420

CTTGAAAAGC TGGACCAATA GCAAGGTAAG TTTGCTTTTC TTACCAAATA GGAGAGGTGC    6480

CTGTCCCAAA GTTGGGGACT CTCCAGGAAC ATGGTAGGAC TGATAACCAT TGTTCACATC    6540

AATAGAAGTG CTATATTACA AGTGGTGGGA AGATGAACAC CATTTCCTGG CGAGTAGAGG    6600
```

-continued

```
ACCTGGTAGT GGCAGGGAAG GCTGCTTGGA CTATCACTGG GTCCTAGAAT TCCTATTCTT      6660

AATTGAGTAT TCTTCAATAA TATTTTTATA CATGCCTACC TGCTAAAGAT TTTTTTGAAC      6720

ATGCACTGAC TATATATGCA TATTTATGAG TTTATGGTAT ACTCTTGTCA ATTCTTATAC      6780

TTTAGATTAG TAAACCTCAA ATTCTTTCTC ATATAGTATG AAATATTACA GCAGTTAATA      6840

TTTTCTTTCT GCACATACAT GAATGTTCTT GCATCCCTGT TAGAGTTCAT CTATGCTCCT      6900

TCAGAGACCA CAAGCCCAAA GACTAGCAGT CCACTCTCTC TGAATATAGG AAAGATATGA      6960

GTAGAAAGAA GGATTCCTGT TCAGATTGTG AAAAAGGAAG TGGAAATGGA GGTGCAGGAG      7020

ATGCTGAGAG ATCTCAGGTG CTAACTGGAC ACTTGCAATG TCAGGAGAGG AAAATTTTAA      7080

CCTGGATTGG GGAAATGGTT CTTCCATGCC CCTTTGCAAT AAGTAACACT GTACCTGAAG      7140

AGAGGGTAAG CAGCAGAAAC AATGGTCCCA GCTGATAACT AGTGACCTGG TGTCCTAATG      7200

ATCAGGGGGC TGGTGCAGTT GACGCTAAAG GGGACAGGGG TCCCAGCTCT CCCATCCTCA      7260

CCCCCACTCT CCACTATCCT CACATATCTG GTTGTCTTTT TTCTCCCTAG GTGTCACCCG      7320

ACCTCAGTGA AGTCTTTGAT GTTTCTGAGA GGCAGACTCC CATGTGGTCC CAGATCCTTG      7380

GTCCATGGAT GACACCACCT TCCCATGCTT CCTTGCATTA GGCTTTCTAA ACCCGGAGCC      7440

CCTTCAAACT TCCAATAAAG GGATCATTTT CTGCTTTATC TGCTTTTGGC TCCAGTGATC      7500

TCTGAATTCC TAGTGGCTCA AGGGGCGTGA GGTCATTTCT GATAAAAATG GTTTTGGAAG      7560

AAAAGAATGG GATATTTTTT AAGCATTAGG GAGAATAGCA ATCAAAGCCA CATTTCTAGA      7620

TGTATTGATA GAAATCCAAC ACTAAAAACA AGATGCTATT ACTCTGCCAG GCACACATCT      7680

ACTTCCTGAT GCCAACCCTA AAGTCTCTCG TGACCTCTGT ACTAACAGGA CCCCAGGATC      7740

TAACAGTCCC CCAGAAAGAA CAGAGAAAAT GTATTGCAAC AAGCCCTAGG AAAGTCCCTG      7800

ATCTACTAGT GCCATGAGTA TTCCCCAAGT CCACAGCAGC ATATCTCTTC ACTTAGCTTA      7860

AGAACTGTCC TACTCCTACA GCATACATTT AGATGCAATC ACACCAAAGA GTGATATGTC      7920

AAGTCTCCAC CACTTCAGCA AGAGTGAGTG GATTTAAAAA TGTTATCTGT GATGGAAAGA      7980

CCAGACGACC AGGCCAGAGT CTTGGGGCAG GTGGTGTGTT AATAATAGAA ATTCTACTCC      8040

TTTTATGCCC TTTCACCCTT TATTCTAAGG ATGATTCCAG GGAAAGCCAA ACATCCAGGA      8100

GAAGAAGCCA ACATAGAGGA ATAAGAAAAA TCACTAGTCT AGGAATAAGA GATCTGGATT      8160

CCATTCTAGC TCTGTTTTAA GAACTAGTAT ATCTTTAATT AAATCTTTTC TTTCCTGCAA      8220

GCTT                                                                  8224
```